US 10,052,113 B2
(12) United States Patent
Turner et al.

(10) Patent No.: US 10,052,113 B2
(45) Date of Patent: Aug. 21, 2018

(54) MEDICAL ALIGNING DEVICE

(76) Inventors: Nicholas Robert Turner, Gloucester (GB); Robert Michael Wozencroft, Surrey (GB)

(*) Notice: Subject to any disclaimer, the term of this patent is extended or adjusted under 35 U.S.C. 154(b) by 1968 days.

(21) Appl. No.: 12/666,591

(22) PCT Filed: Jun. 25, 2008

(86) PCT No.: PCT/GB2008/002244
§ 371 (c)(1),
(2), (4) Date: May 27, 2011

(87) PCT Pub. No.: WO2009/001109
PCT Pub. Date: Dec. 31, 2008

(65) Prior Publication Data
US 2011/0257657 A1    Oct. 20, 2011

(30) Foreign Application Priority Data
Jun. 25, 2007    (GB) .................................. 0712247.6

(51) Int. Cl.
*A61B 17/17* (2006.01)
*A61B 17/00* (2006.01)
*A61B 17/88* (2006.01)

(52) U.S. Cl.
CPC ........ *A61B 17/175* (2013.01); *A61B 17/1721* (2013.01); *A61B 17/8866* (2013.01); *A61B 2017/00469* (2013.01)

(58) Field of Classification Search
CPC .............. A61B 17/1721; A61B 17/175; A61B 2017/00469

USPC ..................................................... 606/96, 103
See application file for complete search history.

(56) References Cited

U.S. PATENT DOCUMENTS

| 2,181,746 | A | * | 11/1939 | Siebrandt | ............... | A61B 17/17 |
| | | | | | | 408/115 R |
| 5,284,482 | A | * | 2/1994 | Mikhail | ............. | A61B 17/1659 |
| | | | | | | 606/86 R |
| 5,314,429 | A | * | 5/1994 | Goble | ................ | A61B 17/1714 |
| | | | | | | 128/898 |
| 6,196,969 | B1 | * | 3/2001 | Bester | ................ | A61B 17/0206 |
| | | | | | | 600/219 |
| 7,488,325 | B2 | * | 2/2009 | Qian | .................... | A61B 17/175 |
| | | | | | | 408/115 R |

(Continued)

FOREIGN PATENT DOCUMENTS

EP          1772106 A1    4/2007
JP       2007512097 A    5/2007
(Continued)

OTHER PUBLICATIONS

Japanese Office Action; Japanese Patent Office; Japanese Patent Application No. 2013-258082; dated Jan. 26, 2015; 5 pages.

(Continued)

*Primary Examiner* — Nicholas Plionis
(74) *Attorney, Agent, or Firm* — Taft Stettinius & Hollister LLP

(57) ABSTRACT

A device (1) for aligning a guide wire with a bone, comprising: an attachment means (2) reversibly attachable to a bone; an alignment means (31) connected to the attachment means, the alignment means being moveable so as to locate a portion of the bone for insertion of the guide wire. A method for aligning a guide wire with a bone.

23 Claims, 26 Drawing Sheets

(56) References Cited

U.S. PATENT DOCUMENTS

2005/0245936 A1    11/2005  Tuke et al.
2006/0081553 A1*  4/2006  Patterson ........... A61B 17/1728
                                                                  215/252

FOREIGN PATENT DOCUMENTS

WO          2005051209 A1    6/2005
WO      WO 2007039647 A1 *  4/2007  ............. A61B 17/28

OTHER PUBLICATIONS

Japanese Office Action; Japanese Patent Office; Japanese Patent Application No. 2010-514117; dated Nov. 10, 2014; 11 pages.
Japanese Office Action; Japanese Patent Office; Japanese Patent Application No. 2010-514117; dated Jul. 27, 2015, 2015; 11 pages.

* cited by examiner

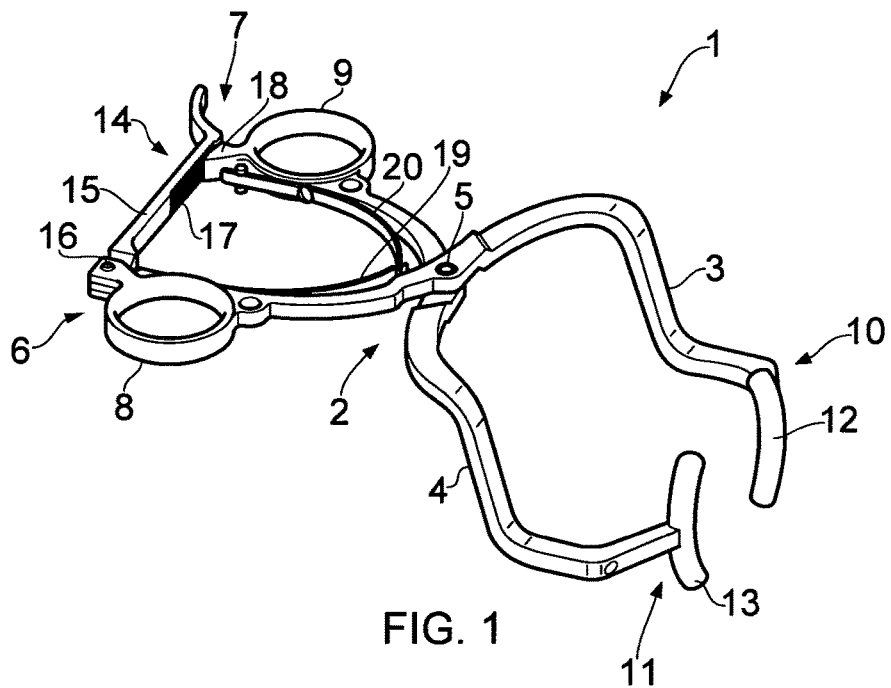
FIG. 1
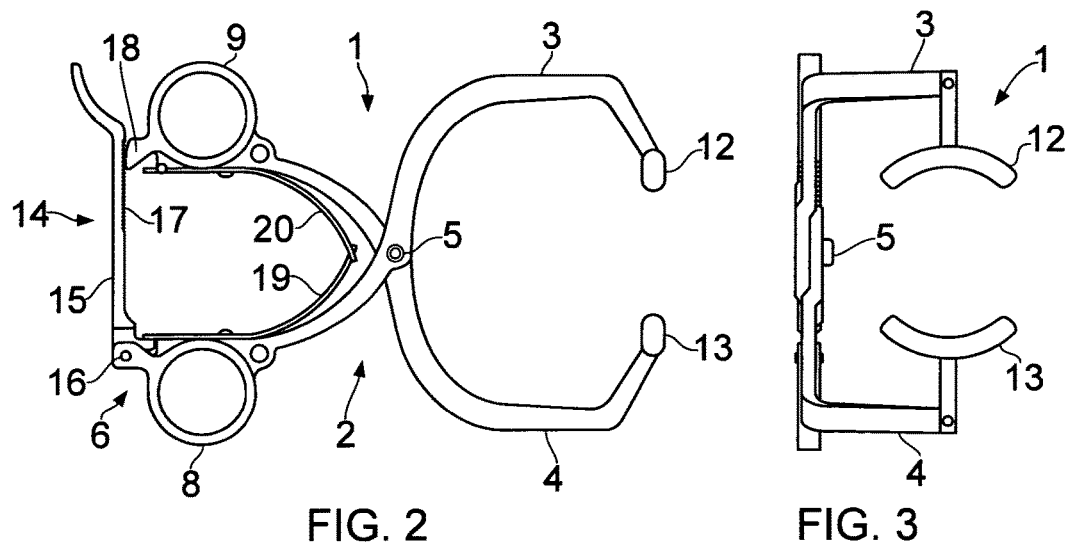
FIG. 2    FIG. 3
FIG. 4

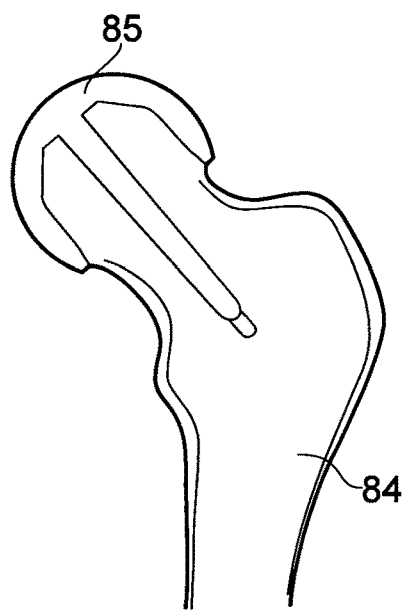
FIG. 16
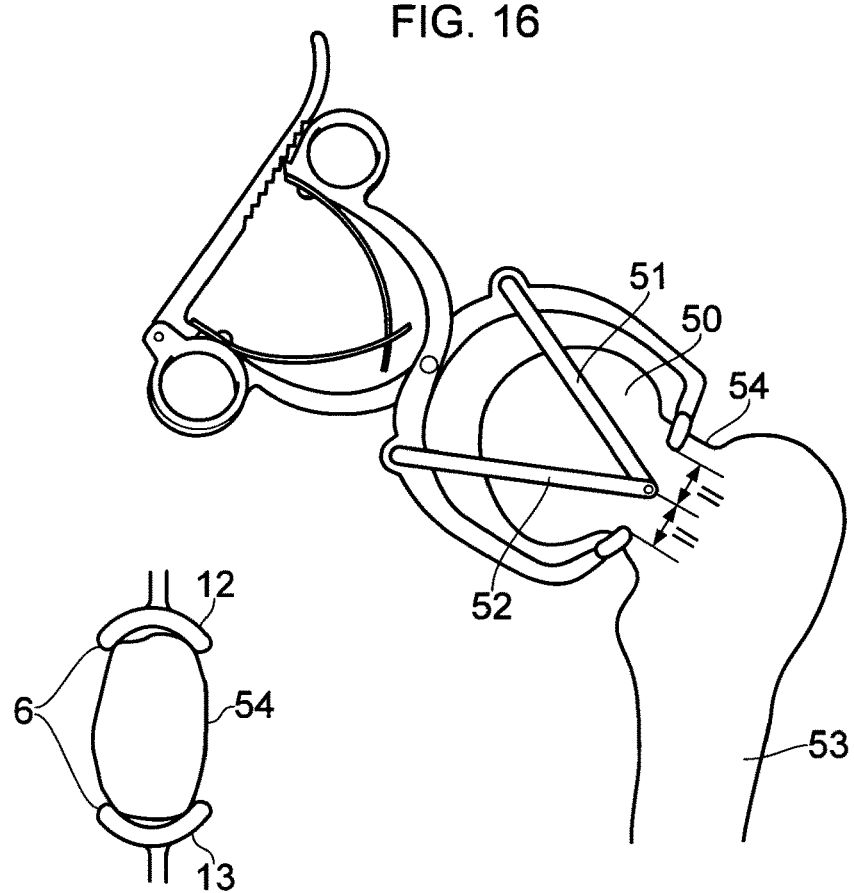
FIG. 12
FIG. 11

MEDICAL ALIGNING DEVICE

This application is a U.S. National Phase filing of International Application No. PCT/GB2008/002244 which claims priority to G.B. Provisional Patent Application No. 0712247.6 filed Jun. 25, 2007, titled "Medical Aligning Device". Both applications are herein incorporated by reference.

The present invention relates to medical devices, in particular devices for aligning guide wires with respect to bones. The present invention also relates to a method of aligning and inserting a guide wire into a bone.

Total hip replacements may fail prematurely due to excessive wear, particularly in active patients. Hence hip resurfacing, using metal on metal bearings, is increasingly being used with good results. Resurfacing preserves the patient's natural femoral neck and part of the femoral head. Accordingly, accurate positioning of the implant components is essential to preserve the integrity and strength of the natural bone. On the rare occasion that metal on metal resurfacings fail, it is mainly because of fracture of the femoral neck or loosening of the femoral component, which may result from poor surgical technique with notching of the femoral neck or incorrect angular positioning of the femoral component.

During the resurfacing operation, preparation of the femur starts with the positioning and drilling of a guide wire through the femoral head and into the neck. Guide wire position is critical because it will define the position and angle of the femoral component relative to the patient's femur. Clearly, it is best for the surgeon to position the guide wire correctly on the first attempt. Once the guide wire is inserted, its position may be verified by rotating a stylus around the femoral neck and the appropriate head component size is identified. The guide wire is then over drilled with a cannulated drill to increase the hole size. A guide rod is then inserted into the hole and used to guide a rotating cylindrical cutter to shape the femoral head into a cylinder. This is the stage in the operative procedure where notching of the femoral, neck can occur due to incorrect positioning or over sailing of the cylinder cutter. A face cutter is then used to resect the unwanted bone. The guide rod is used to guide a rotating chamfer cutter to chamfer the proximal end of the cylinder. This procedure ensures that the implant component fits exactly to the bone.

The femoral head cannot be used as a positioning reference when placing the guide wire, because it is invariably misshapen in varying degrees due to the onset of arthritis. A preferred reference to use is the femoral neck, as this is where notching must be avoided, but this can also be partially misshapen due to osteophytes.

Due to anxiety about notching the femoral neck and the smaller size of the neck relative to the femoral head, it is generally accepted that the best position for the guide wire and hence the femoral implant stem is in the exact centre of the femoral neck. This is often hard to determine because the neck cross section is not circular.

In addition to the guide wire being placed centrally in the neck, there are two important angles of the femoral implant axis relative to the femur which are described in different planes. Observed in the frontal (or coronal) plane on a frontal X-ray, varus/valgus angle is the angle between the shaft of the femur and the implant axis. The appropriate angle is somewhat patient specific, but generally within the range 135-145 degrees. The axis of the natural femoral neck is more varus (or more horizontal) and is difficult to judge because it tapers outwards towards the shaft of the femur. It is therefore erroneous to reference the natural neck angle as the appropriate angle for the implant axis. Excessive varus positioning of the implant is considered to be the second most contributory factor (after notching) towards femoral neck fracture and femoral component loosening.

Observed in the horizontal (or transverse) plane, version angle is a forward or backward angulation of the implant axis relative to the shaft of the femur. It is generally not apparent on X-ray but can be judged intra-operatively by observing the underside of the femoral neck. The appropriate angle is also patient specific but generally within the range 15-25 degrees. In this case, the surgeon generally tries to align the implant axis with the patient's natural anteversion angle.

It is generally accepted that a resurfacing head implanted with the appropriate varus/valgus and version/anteversion angles without notching of the femoral neck will have a good chance of success. However this goal is becoming more difficult to achieve, especially due to the limitations of minimally invasive surgery. There is an increasing trend towards minimally invasive surgery in hip resurfacing which reduces the amount of exposure, access and visibility to the femoral head and neck. It is more difficult for surgeons to detect and correct errors using their judgment, with reduced access and visibility. Therefore they are dependent on the effectiveness of the surgical instrumentation.

A number of devices exist to facilitate positioning of the guide wire and hence the femoral implant component. Early devices used a pin in the lateral femur to help determine angular position and a probe rotating around the neck to avoid notching. The requirement for a pin in the latera femur means that such devices are not suitable for minimally invasive surgery because there is insufficient access to insert a pin laterally.

Later devices follow the trend towards minimally invasive surgery. The devices tend to fall into three categories, namely clamp type, ring type and adjustable platform type devices. Clamp type devices comprise a drill guide and opposing jaws that attach to the femoral neck. A common problem with clamp type devices is that they tend to follow the natural femoral neck angle, which, as already described, is not the correct angle for the femoral implant axis. An attempt to overcome this has been made by replacing a symmetrical jaw clamp with an offset jaw clamp. Offsetting the jaws allows the device to be placed in a more valgus angle relative to the natural neck. However an offset jaw clamp is inherently unstable because the jaws do not directly oppose one another. It is therefore less effective as a clamp.

In both the above types of devices, it is a difficult task for the surgeon to decide varus/valgus and version angles simultaneously, particularly considering that these angles are judged in two different anatomical planes.

Ring type devices comprise a drill guide and a partial or complete ring which is placed around the femoral neck, where the diameter of the ring corresponds to the femoral implant component internal diameter. These devices are not as stable as clamp type devices because they do not attach to the femoral neck. Furthermore, varus/valgus and version angles must also be judged and fixed simultaneously by the surgeon when using such devices. Consequently, they present similar problems to those encountered with clamp type devices.

Adjustable platform type devices comprise a drill guide and a platform that is fixed to the femoral head and from which adjustments to position and angles are made and verified with a rotating stylus. Such devices provide a stable platform to work from, but have the disadvantage that the surgeon still has to judge and fix varus/valgus and version angles simultaneously.

Accordingly, the present invention aims to maximise the accuracy of guide wire placement which in turn optimises the positioning of the final femoral component. The present invention also aims to provide guide wire placement devices that are suitable for use in minimally invasive surgery.

According to a first aspect of the present invention, there is provided a device for aligning a guide wire with a bone, comprising:
an attachment means reversibly attachable to a bone;
an alignment means connected to the attachment means, the alignment means being moveable so as to locate a portion of the bone for insertion of the guide wire.

An advantage of the present invention is that it increases the accuracy of guide wire placement. Consequently, positioning of the final femoral component is optimised, significantly reducing, if not eliminating, failure of the metal on metal resurfacing. In addition, it does not require a lateral or posterior targeting pin and therefore is suitable for minimally invasive surgery since it can be operated through a reduced incision.

Devices according to the present invention improve upon existing devices by enabling the alignment means to move independently with respect to the attachment means. This means that the device can be securely attached to the femoral neck, for example with symmetrical, directly opposing jaws, which provide a stable platform to work from. The varus/valgus angle is then set via a separate adjustment via the alignment means.

The alignment means may be reversibly connected to the attachment means.

The alignment means may receive a guide wire, in use.

According to some embodiments of the present invention there is provided a device wherein the alignment means comprises:
an alignment guide for receiving, in use, at least one of a goneometer and a guide wire; and
a support arm connected to the attachment means, wherein the alignment guide is moveably connected to the support arm.

The alignment guide may be reversibly connected to the support arm.

The support arm may be reversibly connected to the attachment means.

The support arm may be pivotally connected to the attachment means.

The alignment means may comprise a centring mechanism for locating the centre of the bone.

In some embodiments of the invention, the device has a centring mechanism to place the guide wire in the centre of the femoral neck at all times irrespective of varus/valgus adjustment. In those embodiments of the invention that comprise a centring mechanism, the act of attaching the device to the femoral neck establishes the neck centre via the centring mechanism and makes the device stable. Thereafter, varus/valgus and version angles are independently adjusted. This is more effective and more accurate than previous devices which are unstable until both angles are fixed. In addition, such prior art devices also have the disadvantage that a change to one angle affects the other angle.

The centring mechanism may be reversibly connected to the attachment means.

The centring mechanism may comprise two moveable arms, each arm having a proximal end and a distal end, the arms being pivotally connected together at their distal ends, the arms being pivotally connected to the attachment means at their proximal ends, and wherein, in use, the pivot connection between the distal ends of the arms locates the centre of the bone.

The alignment guide may be pivotally connected to the distal ends of the centring mechanism arms.

The attachment means may be a clamp. The attachment means may be a scissor clamp.

The clamp may comprise at least two jaws. The clamp may comprise two jaws. The clamp may comprise a plurality of jaws. The at least two jaws may be opposed.

The clamp may comprise a self-locking mechanism. The self-locking mechanism may be a ratchet mechanism having a release means for unlocking the clamp.

The clamp may comprise a resilient means for biasing the jaws apart. The resilient means may be a spring.

The attachment means may comprise two arms that are pivotally connected along their length, each arm having a proximal end and a distal end, the distal ends being attachable to a bone, the proximal ends enabling a user to reversibly attach the distal ends to the bone.

The alignment guide may comprise a drill guide.

Devices according to embodiments of the present invention may further comprise a fixation means. The fixation means may comprise at least one retractable spike. The fixation means may comprise a retractable spiked tube.

According to a second aspect of the present invention there is provided a method of aligning a guide wire with a bone, comprising the steps of:
providing a device according to the first aspect of the present invention and a power source;
attaching the attachment means to a bone;
moving the alignment means so as to locate a portion of the bone for insertion of the guide wire; and
inserting the guide wire into the bone using the power source.

According to a third aspect of the present invention there is provided a method of aligning a guide wire with a bone, comprising the steps of:
providing a device according to the first aspect of the present invention and a power source;
attaching the attachment means to a bone;
moving the alignment means so as to locate a portion of the bone for insertion of the guide wire;
attaching a goneometer to the alignment guide so as to indicate the eventual position of the guide wire in the bone;
attaching a guide wire to the alignment guide; and
inserting the guide wire into the bone using the power source.

The goneometer may be detached from the alignment guide before the guide wire is attached.

The power source may be a rotary power source. The power source may be a drill.

The device/method may be applied to any suitable bone. The bone may be a femur.

Reference will now be made, by way of example, to the accompanying drawings, in which:

FIG. 1 is an isometric view of a device according to an embodiment of the present invention;

FIG. 2 is a top view of the device shown in FIG. 1;

FIG. 3 is an end view of the device shown in FIG. 1;

FIG. 4 is a side view of the device shown in FIG. 1

FIG. 11 is a side view of a device according to an embodiment of the present invention in place on a femur;

FIG. 12 is a cross-section through a femoral neck;

FIG. 16 is a section through a femur having a resurfacing head attached;

Figure 5:
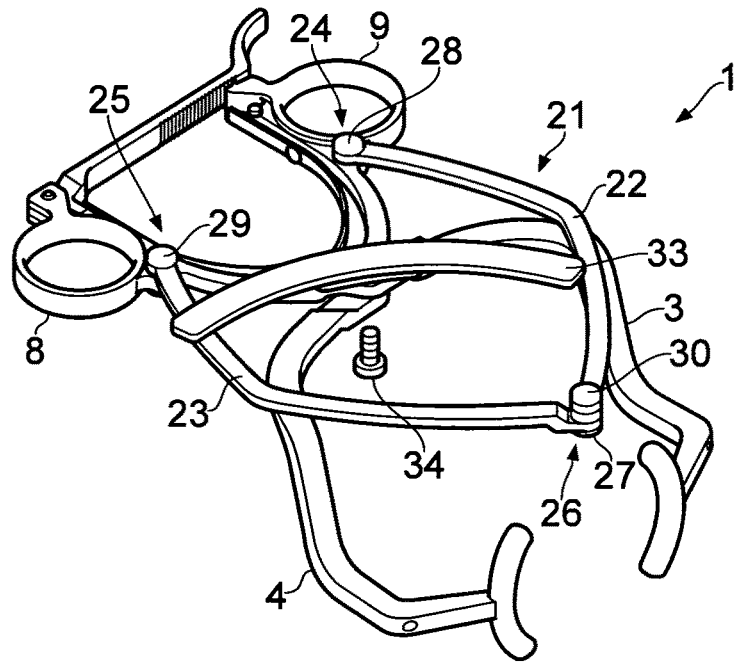
FIG. 5 is an isometric view of a device according to another embodiment of the present invention.

FIGS. 1 to 10 show components of a device (1) according to some embodiments of the present invention. As shown in FIGS. 1 to 4, the device (1) is in the form of a scissor clamp (2) with a ratchet locking mechanism (14). The clamp (2) comprises two arms (3,4) that are connected together by a pivot (5). In the embodiments shown, the pivot (5) is near to the mid-point of each arm (3,4). Each arm (3,4) has a proximal end (6,7) and a distal end (10,11). Disposed at the proximal end (6,7) of each arm (3,4) is a finger grip (8,9) enabling a user to grip the clamp (2). In the device shown, the finger grips (8,9) are closed hoops, although any suitable grip is envisaged. Disposed at the distal end (10,11) of each arm (3,4) is a jaw (12,13) for attaching the device to a bone. Alternative embodiments may have a plurality of jaws.

As shown in FIG. 2, when viewed in the horizontal plane, each arm (3,4) has curved and linear sections forming a distorted S-shape. As shown in FIG. 4, when viewed in the vertical plane, each arm (3,4) has two approximately 90 degree bends between the pivot (5) and the distal end (10,11) such that the main axis of a portion of each arm (3,4) between the proximal end (6,7) and the pivot (5) is parallel to the main axis of a portion of each arm (3,4) near the distal end (10,11). This offset, non-planar structure has the advantage that, in use, the surgeon can manipulate the device so that the jaws (12,13) can be appropriately positioned around and engaged with a bone.

A ratchet locking mechanism (14) is disposed at the proximal end (6,7) of the arms (3,4). The ratchet (14) comprises an arm (15) that is connected to the proximal end (6) of arm (3) by pivot (16). Indentations (17) engage with a complementary protrusion (18) disposed at the proximal end (7) of arm (4), thereby effecting the self-locking ratchet mechanism (14). The ratchet mechanism (14) can be unlocked by moving arm (15) about pivot (16) so as to disengage the protrusion (18) from the indentations (17). Leaf springs (19,20) are attached to arms (3,4) so as to bias the proximal ends (7,8) apart and hence bias distal ends (10,11) apart. As shown in FIG. 2, leaf spring (19) extends towards proximal end (6) of arm (3) and contacts ratchet arm (15) near to pivot (16), thereby biasing arm (15) into a locked position.

FIG. 5 shows the components of FIGS. 1 to 4 in combination with a centring mechanism (21). The centring mechanism (21) has two moveable arms (22,23), each having a proximal end (24,25) and a distal end (26,27). In the embodiment shown in FIG. 5, each arm is curved. However, some embodiments include linear arms (51,52), as shown in FIG. 11. Proximal end (24) of centring arm (22) is pivotally connected to clamp arm (4) by pivot (28), located near to grip (9). Proximal end (25) of centring arm (23) is pivotally connected to clamp arm (3) by pivot (29), located near to grip (8). Distal end (26) of centring arm (22) is pivotally connected to distal end (27) of centring arm (23) by pivot (30).

FIGS. 5 to 10 show an alignment means (31) according to some embodiments of the present invention. The alignment means (31) comprises a centring mechanism (21), an alignment guide (32) and a support arm (33). The support arm (33) is pivotally connected to the clamp (2) by pivot (5). The support arm (33) can be fixed in place using a fixing screw (34) at pivot (5). In the particular embodiment shown, the support arm (33) is crescent shaped. The support arm may be any suitable shape.

Figure 8:
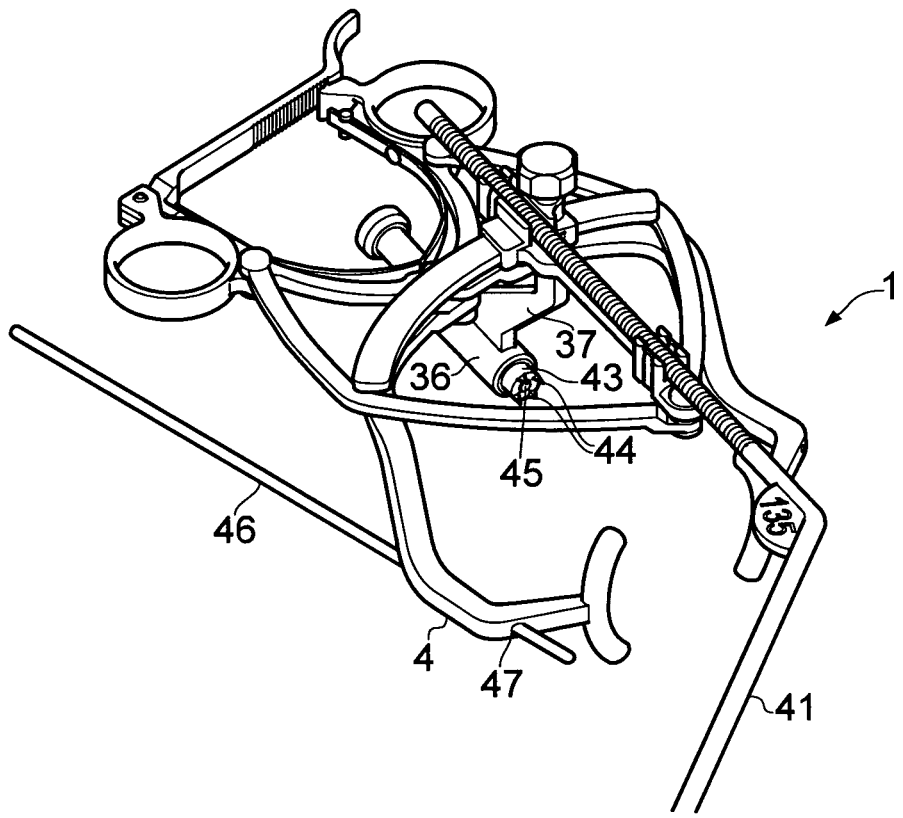
FIG. 8 is an isometric view of a device according to another embodiment of the present invention.

The alignment guide (32) comprises an alignment arm (35) that is connected to an alignment conduit (36) by body (37). Alignment arm (35) has a proximal end (38) that is shaped so as to receive the support arm (33) such that the alignment guide (32) is moveably connected to the support arm (33). The alignment guide (32) can be reversibly locked in position on the support arm (33) by means of locking screw (39) disposed at the proximal end (38) of alignment arm (35). The alignment arm (35) has a distal end (57) that is pivotally connected to the distal ends (26,27) of centring arms (22,23) by pivot (30). The alignment arm (35) has spring clips (40) disposed at the distal end (57) for receiving a goneometer (41,42), as shown in FIGS. 8 and 9.

Figure 8A:
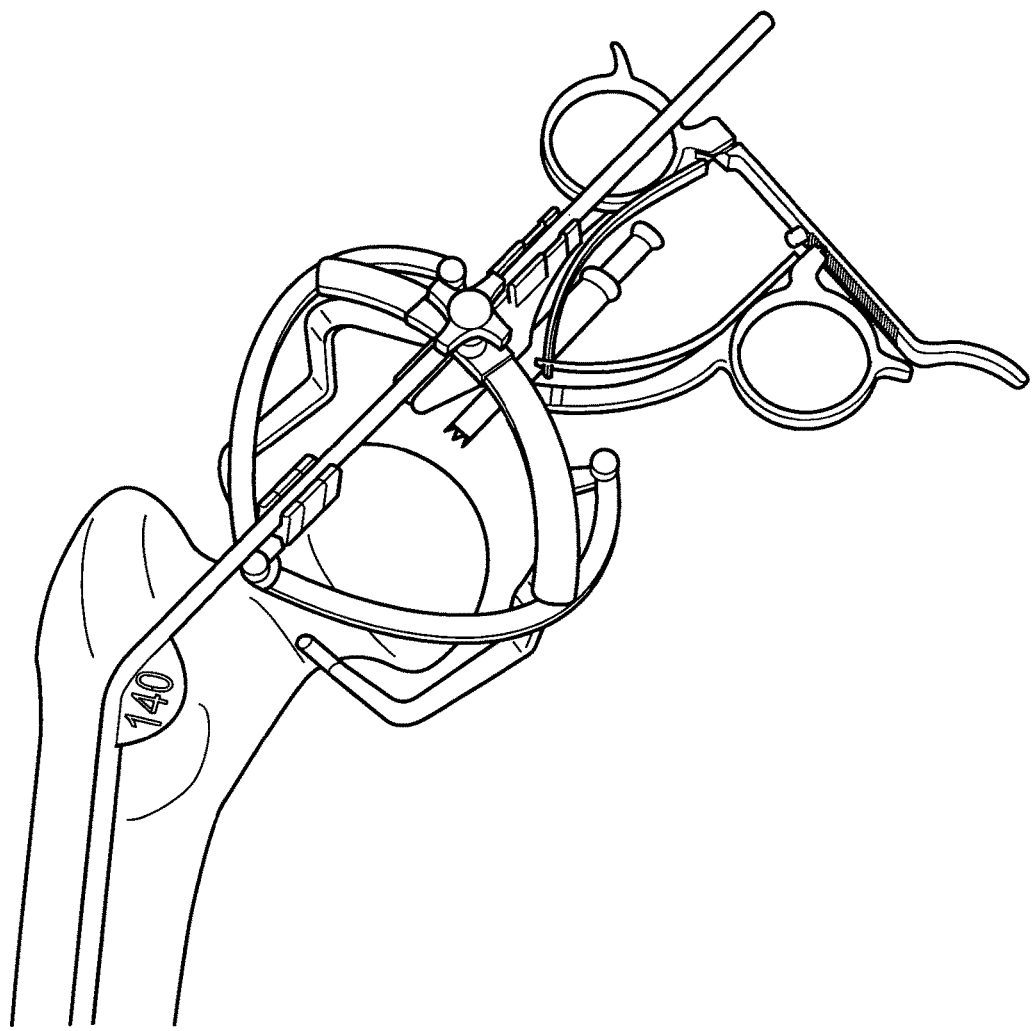
FIG. 8a is a side view of a device according to an embodiment of the present invention in place on a femur.

A goneometer is a separate angle measuring device employed by the surgeon to find the correct varus/valgus angle. Those embodiments of the invention that comprise a goneometer have the advantage that it facilitates hands free use. FIGS. 8, 8a and 9 show two alternative designs of goneometer (41,42). Goneometer (41) of FIGS. 8 and 8a comprises an angled, 'V'-shaped rod that defines the angle between the femoral implant component axis and the femoral shaft. The rod may have any suitable angle. For example, the rod may have an angle of 130 to 140 degrees. The rod may have an angle of around 135 degrees. In use, a surgeon aligns the longer part of the shaft with the femoral shaft by adjusting the alignment guide (32).

Figure 9:
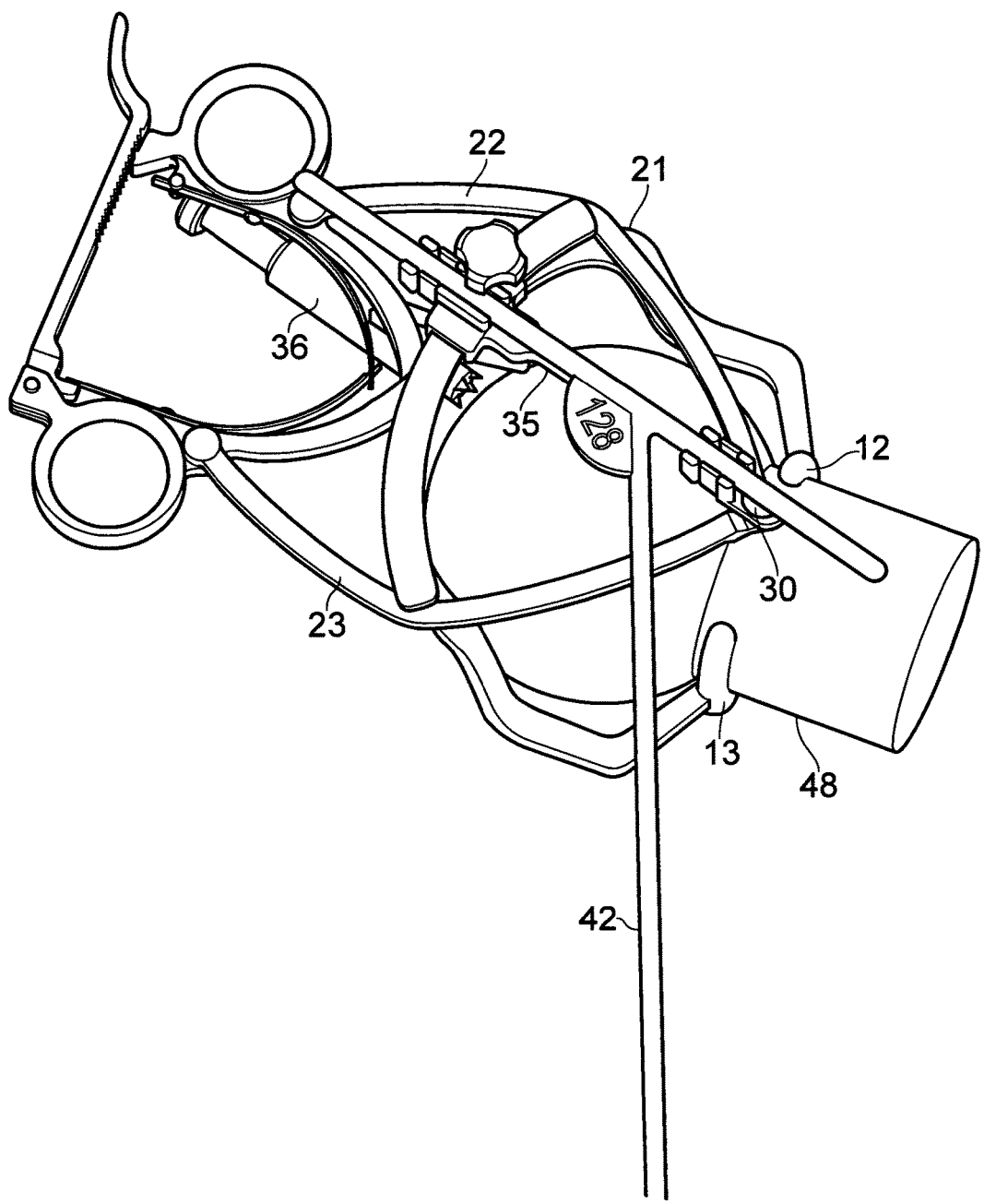
FIG. 9 is an isometric view of a device according to another embodiment of the present invention.

Goneometer (42) of FIG. 9 comprises a distorted 'T'-shaped rod that defines the correct varus/valgus angle from the leg alignment axis, which is a straight line between the centre of the hip and the centre of the knee. The rod may have any suitable reference angle. In the example shown, the reference angle is 128 degrees. In use, the surgeon aligns the intersection of the 'T' rod over the centre of the femoral head and ensures that the distal end of the rod points towards the centre of the knee. The difference between the femur shaft angle and leg alignment axis is 7 degrees, therefore the difference between the angles of the goneometers is also 7 degrees.

Alignment conduit (36) is shaped so as to receive a guide wire. As shown in FIG. 8, in some embodiments of the present invention, the conduit (36) comprises a fixation means (43). In the embodiment shown in FIG. 8, the fixation means (43) is in the form of a cylindrical plunger having a plurality of spikes (44) arranged around a conduit (45) for receiving a guide wire (not shown). In use, the surgeon can advance the plunger from a retracted, disengaged position to an advanced, engaging position in which the spikes (44) engage a bone. The fixation means has the advantage that it provides additional stability to the device.

Figure 6:
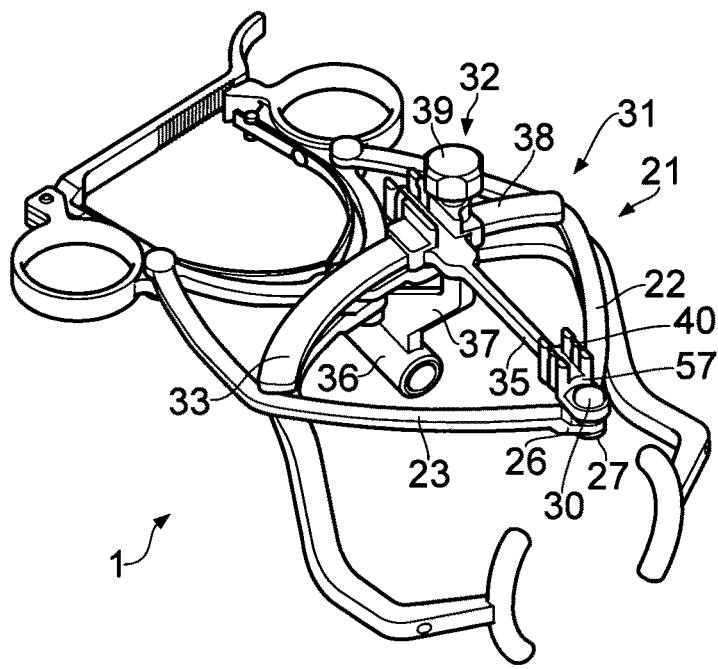
FIG. 6 is an isometric view of a device according to another embodiment of the present invention.
Figure 7:
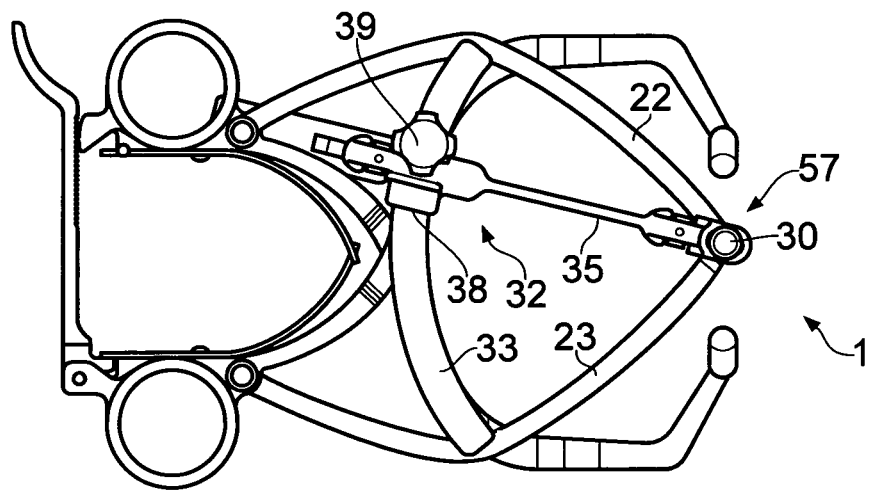
FIG. 7 is a top view of the device shown in FIG. 6.

In an alternative embodiment of the invention (not shown), the alignment means comprises an alignment guide (32) pivotally connected to the centring mechanism (21) as in FIG. 6, but without a support arm (33).

FIG. 8 shows an embodiment of the invention which comprises an additional guide rod (46). In use, the guide rod (46) is received in a conduit (47) in arm (4). In use, the guide rod (46) is aligned parallel to the guide wire, providing the surgeon with an additional point of reference when aligning the device/guide wire.

In an alternative embodiment of the invention (not shown), alignment arm (35) may receive a guide rod like guide rod (46) instead of a goneometer (41,42).

Figure 10:
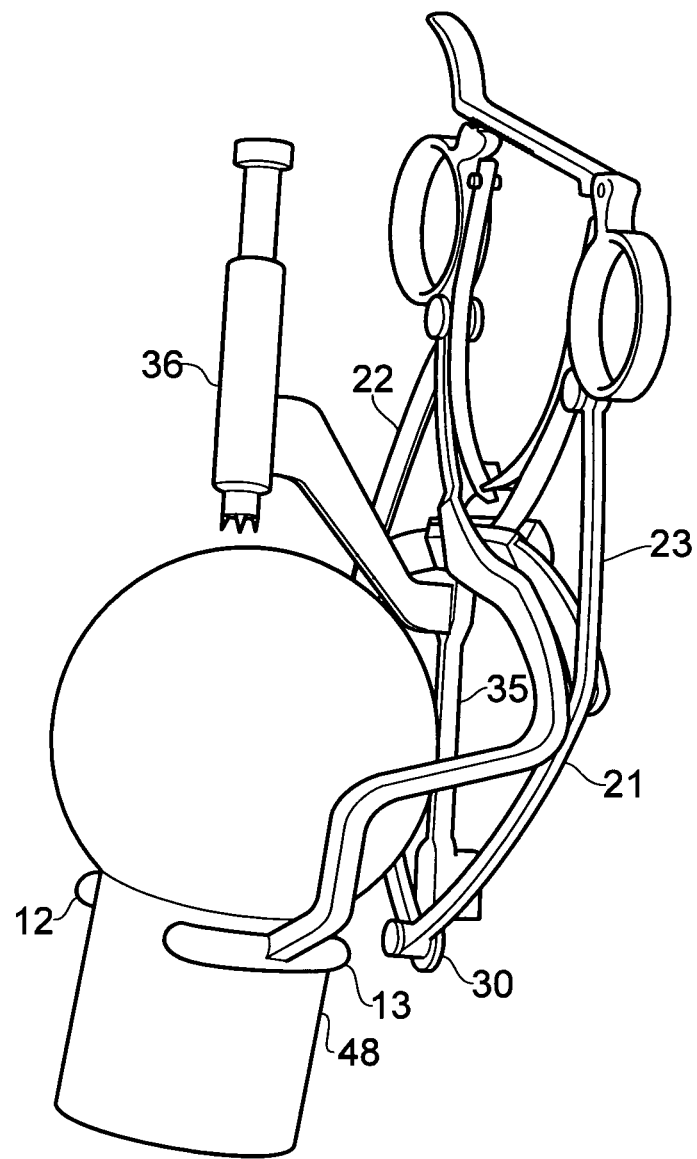
FIG. 10 is an isometric view of a device according to an embodiment of the present invention in place on a femur.

In use, centring mechanism (21) works as follows. As shown in FIGS. 9 and 10, the moveable arms (22,23) are positioned with respect to the jaws (12,13) such that the pivot (30) is naturally aligned with the centre-point of the jaws (12,13) when the jaws of the device are attached to the neck of the femur (48), for example. As a result, the alignment guide is naturally aligned such that the alignment arm (35) and conduit (36), and hence the goneometer (41,42) and guide wire (not shown), are aligned with the centre-point of the jaws (12,13) and hence the centre-point of the neck of the femur, for example.

Figure 13:
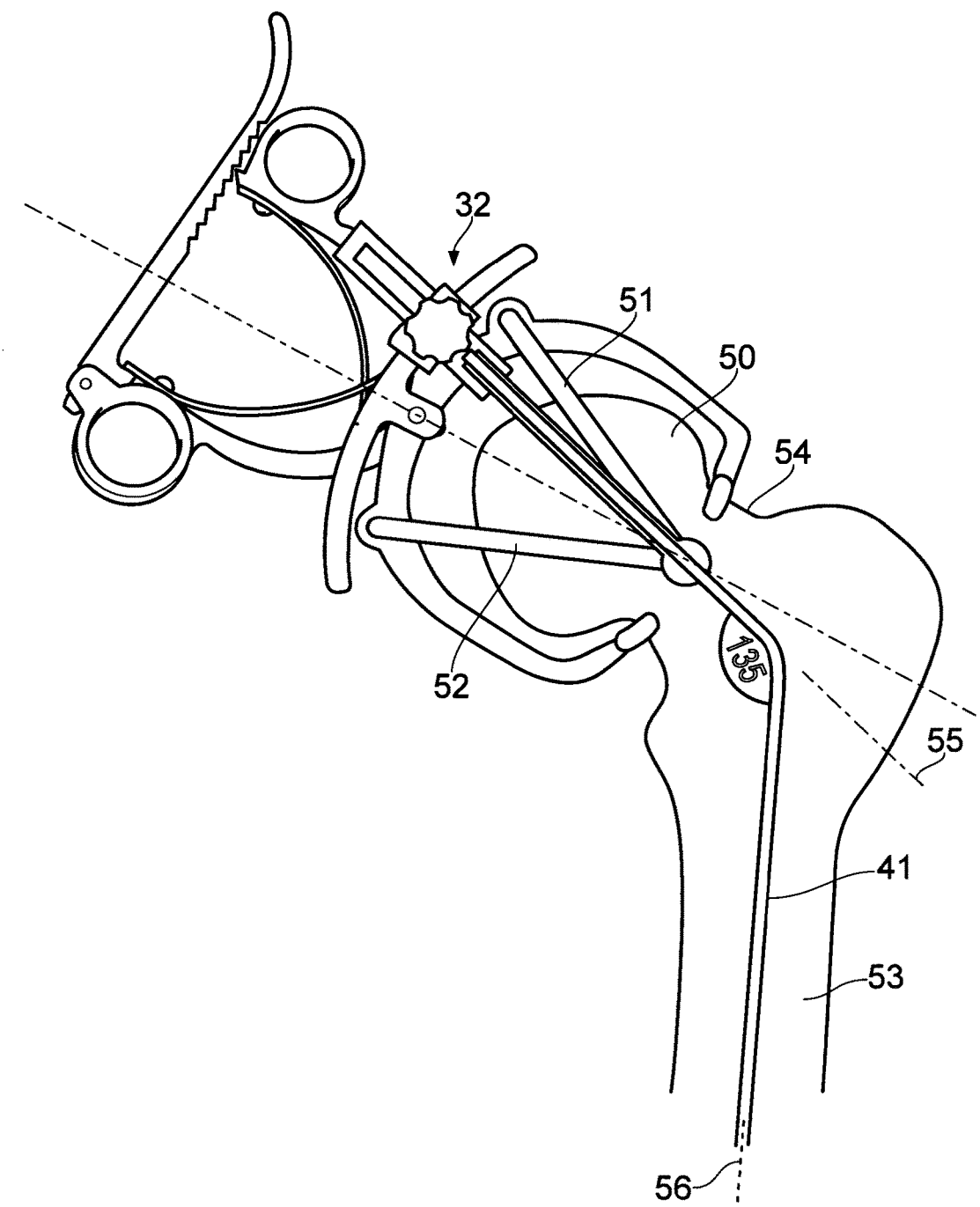
FIG. 13 is a side view of a device according to an embodiment of the present invention in place on a femur.

FIGS. 11 and 13 show a centring mechanism (50) in which the arms (51,52) are linear, instead of curved as in FIGS. 5 to 10. The principle of operation of the centring mechanism (50) is the same as that described above in relation to FIGS. 9 and 10. FIG. 12 shows a cross-section through the neck (54) of a femur (53), with the jaws (12,13) of the device attached to the neck (54) in an opposed position. From FIGS. 11 and 12, it is clear how the centring mechanism (50) locates the centre of the neck (54), in the same way as the device shown in FIGS. 9 and 10.

FIG. 13 shows an assembled device having a linear arm (51,52) centring mechanism (50), comprising an alignment guide (32) as in FIG. 6 (note that the alignment conduit (36) is not shown, for reasons of clarity). The device comprises a goneometer (41), which as shown is aligned with the central axis (55) of the femur neck (54) and the femur axis (56).

Figure 14:
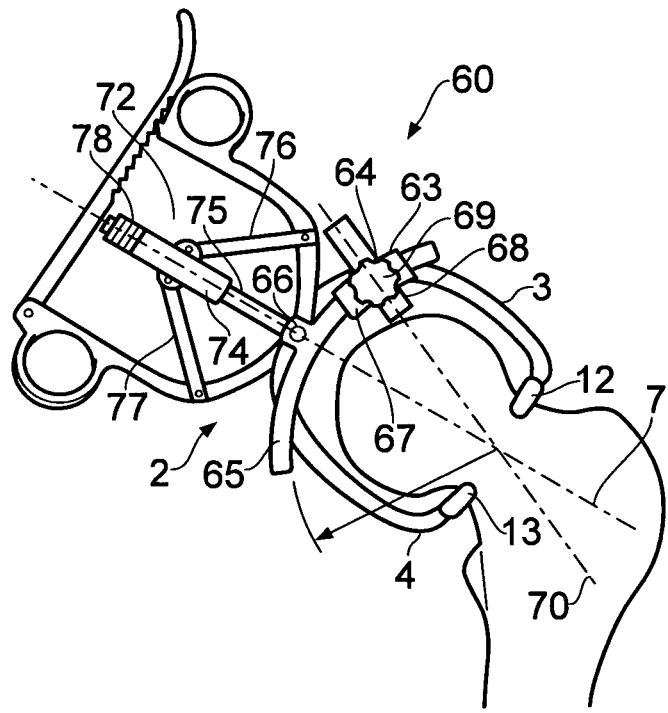
FIG. 14 is a side view of a device according to an embodiment of the present invention in place on a femur.
Figure 15:
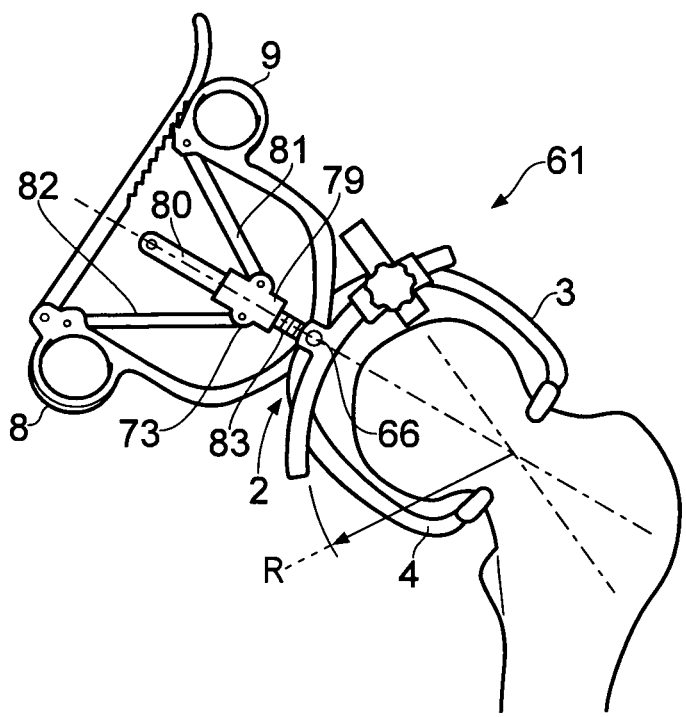
FIG. 15 is a side view of a device according to an embodiment of the present invention in place on a femur.

FIGS. 14 and 15 show two alternative devices (60,61) to those shown in FIGS. 1 to 13. Alignment means (63) comprises an alignment guide (64) and a support arm (65). The support arm (65) is fixedly attached to scissor clamp (2) at fixation point (66). Support arm (65) may be fixed in place by a fixing screw. The alignment guide (64) comprises a body (67) that is shaped so as to receive support arm (65) such that the alignment guide (64) is moveably connected to the support arm (65). Alignment guide (64) comprises an alignment conduit (68) that is connected to body (67). Alignment conduit (68) is shaped so as to receive a guide wire (not shown). The alignment guide (64) can be reversibly locked in position on the support arm (65) by means of locking screw (69) disposed on body (67).

The devices (60,61) of FIGS. 14 and 15 do not have a centring mechanism like that shown in FIGS. 5 to 13. Instead, as shown in FIGS. 14 and 15, the arc of support arm (65) is defined by a radius R such that the main axis (70) of alignment conduit (68) intersects clamp axis (71) at the centre point of jaws (12,13).

The devices (60,61) of FIGS. 14 and 15 have alternative biasing means (72,73) to the leaf springs (19,20) of the devices shown in FIGS. 1 to 13. Biasing means (72) of FIG. 14 comprises a body (74) moveably connected to a rod (75) attached to scissor clamp (2). A first arm (76) is pivotally connected to body (74) at one end and pivotally connected to arm (4) of scissor clamp (2) at the other end near to the fixation point (66). A second arm (77) is pivotally connected to body (74) at one end and pivotally connected to arm (3) of scissor clamp (2) at the other end near to the fixation point (66). A spring (78) is attached to the proximal end of rod (75), such that it biases scissor clamp arms (3,4) apart via body (74) and arms (76,77).

Biasing means (73) of FIG. 15 comprises a body (79) moveably connected to a rod (80) attached to scissor clamp (2). A first arm (81) is pivotally connected to body (79) at one end and pivotally connected to arm (4) of scissor clamp (2) at the other end near to the grip (9). A second arm (82) is pivotally connected to body (79) at one end and pivotally connected to arm (3) of scissor clamp (2) at the other end near to the grip (8). A spring (83) is attached to the distal end of rod (80) near to fixation point (66), such that it biases scissor clamp arms (3,4) apart via body (79) and arms (81,82).

FIG. 16 shows a section through a femur (84) having a resurfacing head (85). Devices according to the present invention enable a surgeon to attach a resurfacing head in the optimal position, as shown in FIG. 16.

Figure 17:
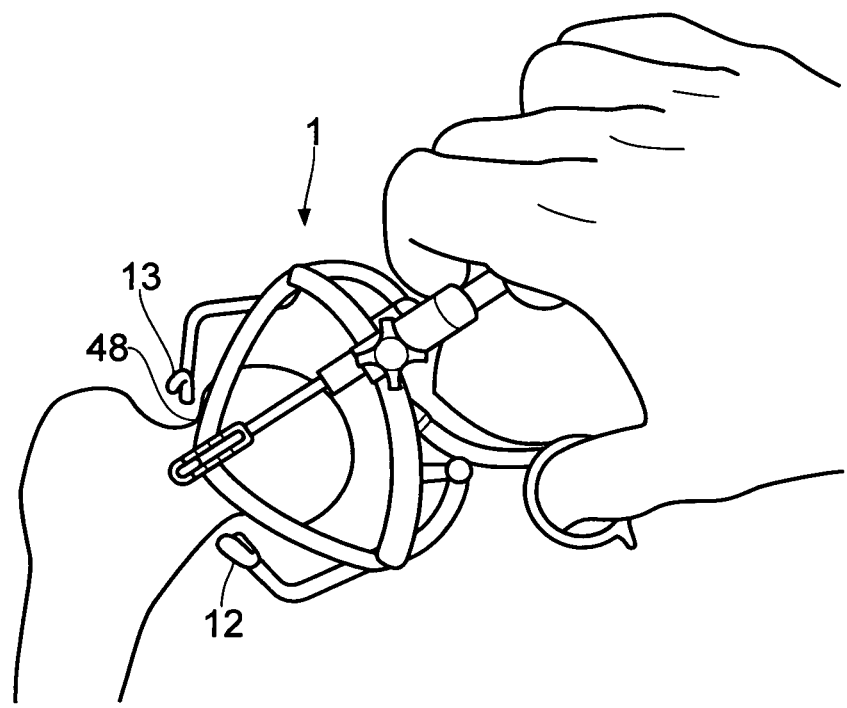
FIGS. 17 to 26 show various stages of operation of a device according to an embodiment of the present invention.
Figure 18:
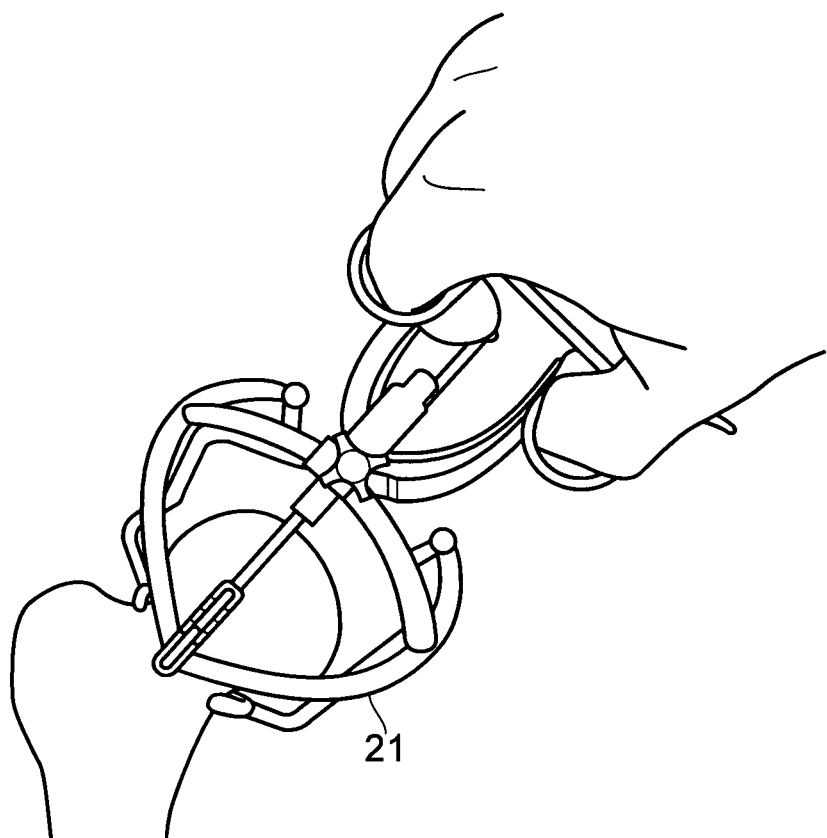

As shown in FIG. 17, with the device (1) in its open position, it is applied to a femur in the anterior-posterior (AP) direction and clamped securely about the femoral neck (48) with the jaws (12,13) superior and inferior (FIG. 18). The self-locking ratchet mechanism (14) maintains a secure grip. The device shown has a centring mechanism (21) to locate the guide wire in the centre of the femoral neck at all times irrespective of varus/valgus adjustment. The simple act of clamping the device to the femoral neck establishes the neck centre via the centring mechanism and makes the device stable.

Figure 19:
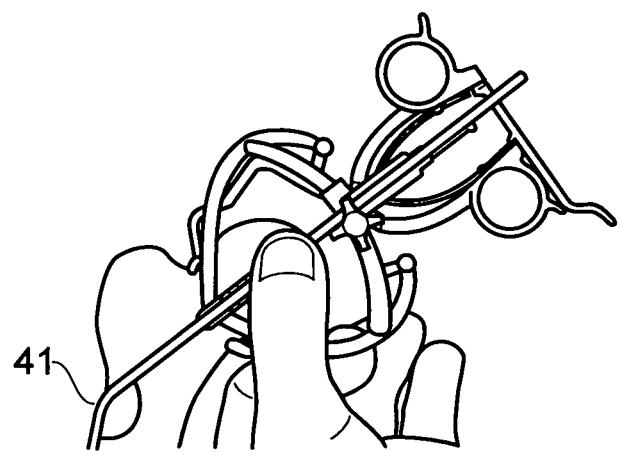

As shown in FIG. 19, the removable goneometer (41) provides additional alignment means and is incorporated within the device, thereby facilitating hands free use and enabling the surgeon to determine the correct varus/valgus angle.

Figure 20:
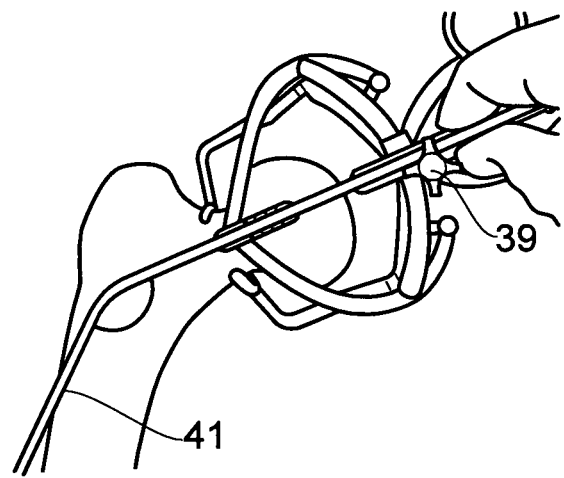
Figure 21:
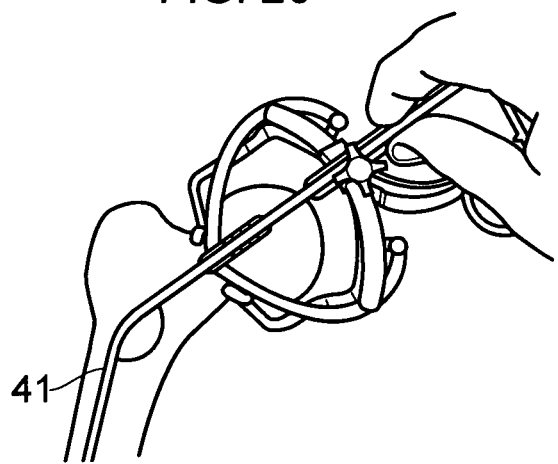

As shown in FIGS. 20 and 21, the varus/valgus angle alignment is adjusted by loosening the locking screw (39) and swiveling the alignment guide with goneometer attached until the main shaft of the goneometer is in line with the femoral shaft. When content with the varus/valgus angle, the surgeon tightens the locking screw (39) leaving the goneometer attached. Note that a useful angle reference may be made from the medial calcar.

Figure 22:
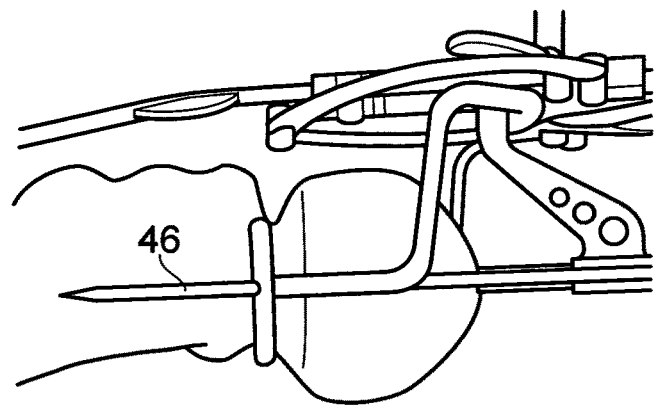
Figure 23:
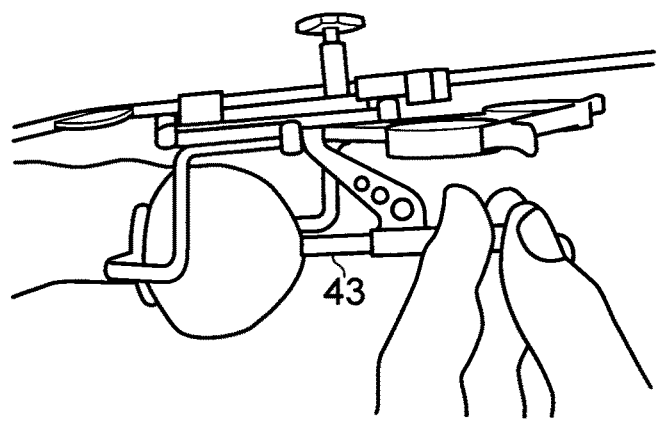

As shown in FIG. 22, an additional guide rod (46) may be inserted into a conduit (47) in the inferior arm. The surgeon can sight along the rod (46), with direct vision of the inferior neck. A guide wire is aligned with the inferior neck by toggling the entire device to select the appropriate anteversion angle. With the device aligned in both planes, the device may be fixed in position. As shown in FIG. 23, spiked plunger (43) is engaged with the femoral head. This may be assisted by the careful use of a hammer.

Figure 24:
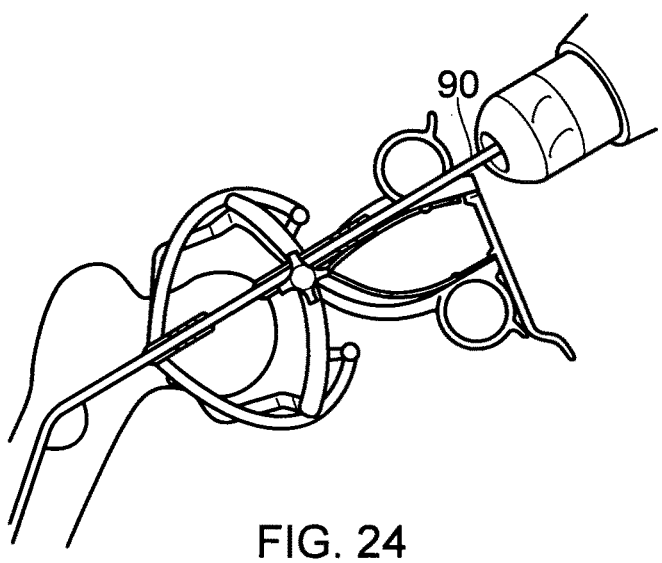
Figure 25:
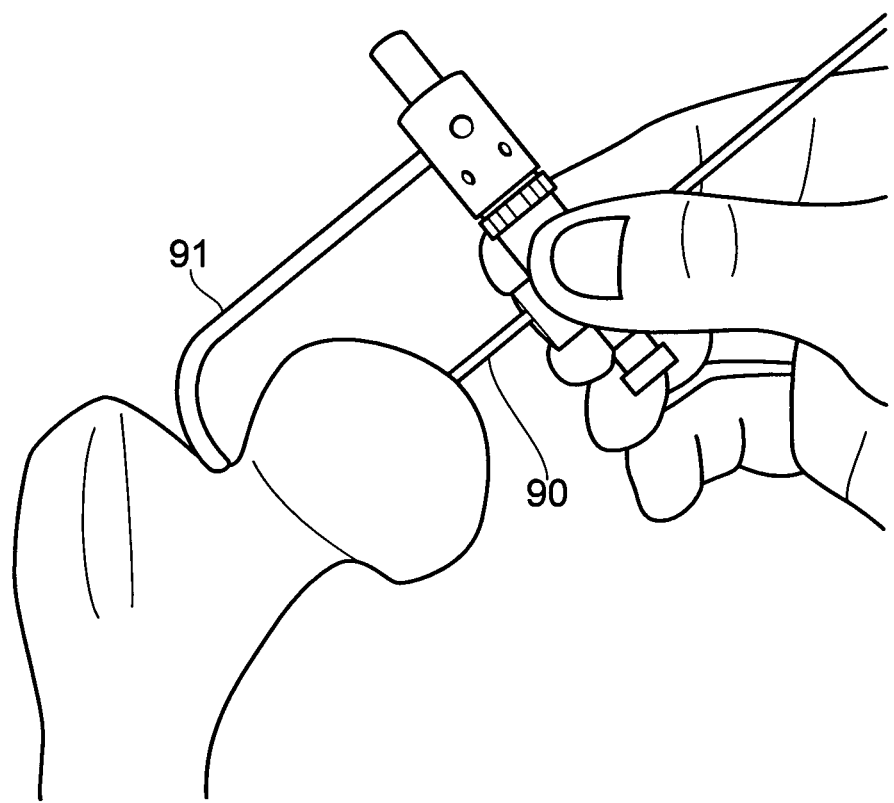
Figure 26:
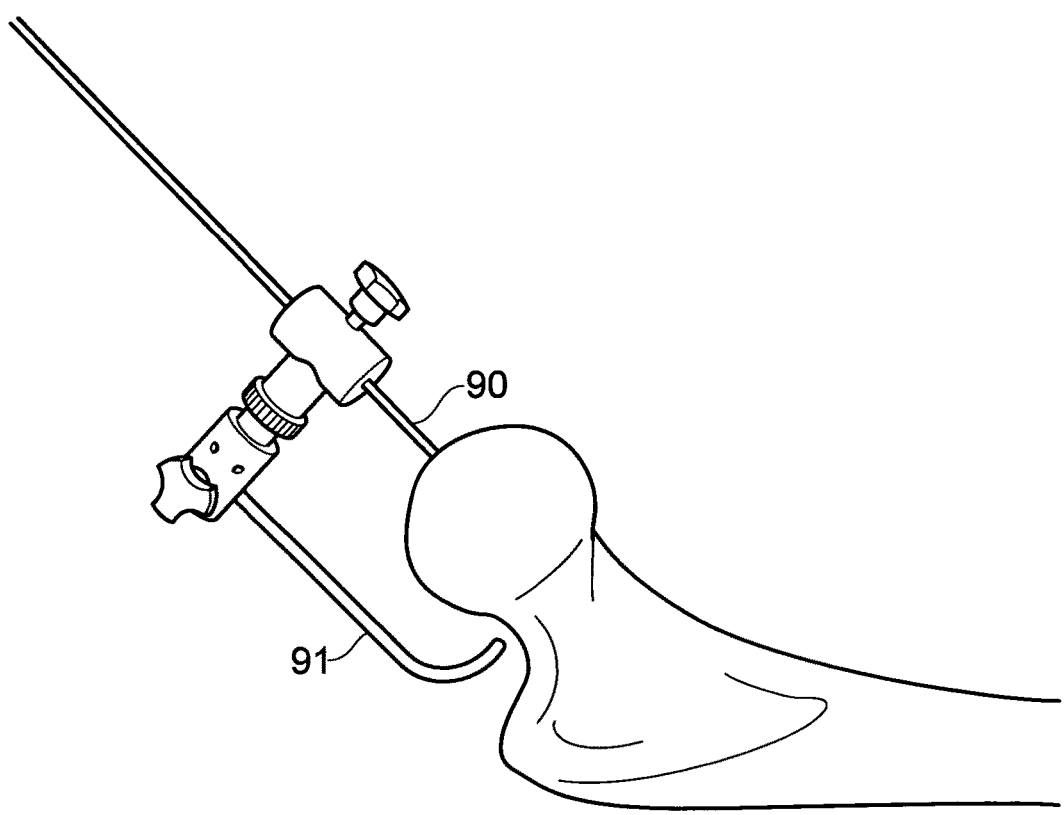

FIG. 24 shows a guide wire (90) being drilled through the drill guide into the femoral head and neck. The device is then removed and the guide wire (90) position may be verified using a conventional stylus (91), as shown in FIGS. 25 and 26. The resurfacing operation is then continued as per normal.

Figure 27:
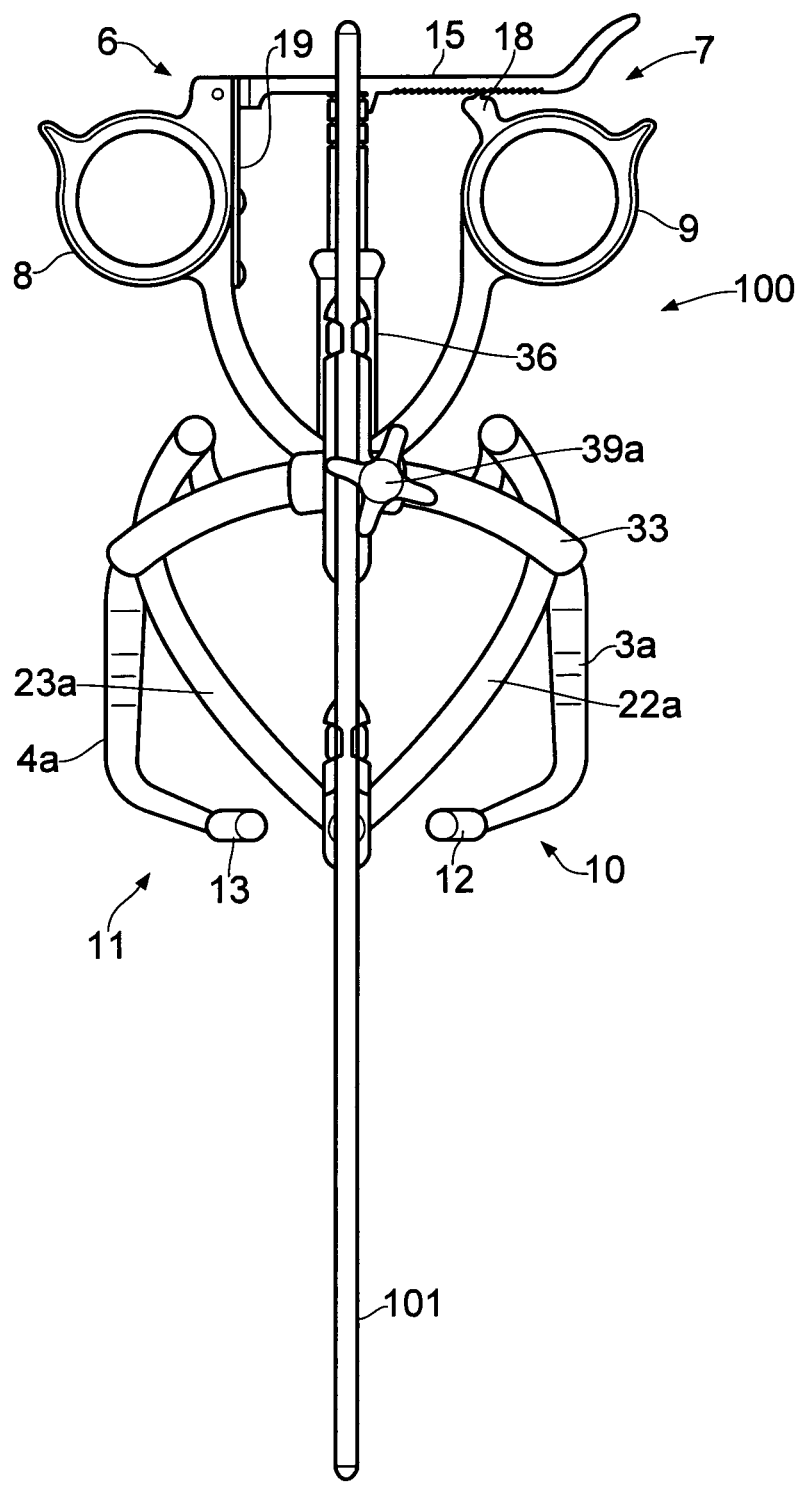
FIG. 27 is a top view of a device according to another embodiment of the present invention.
Figure 28:
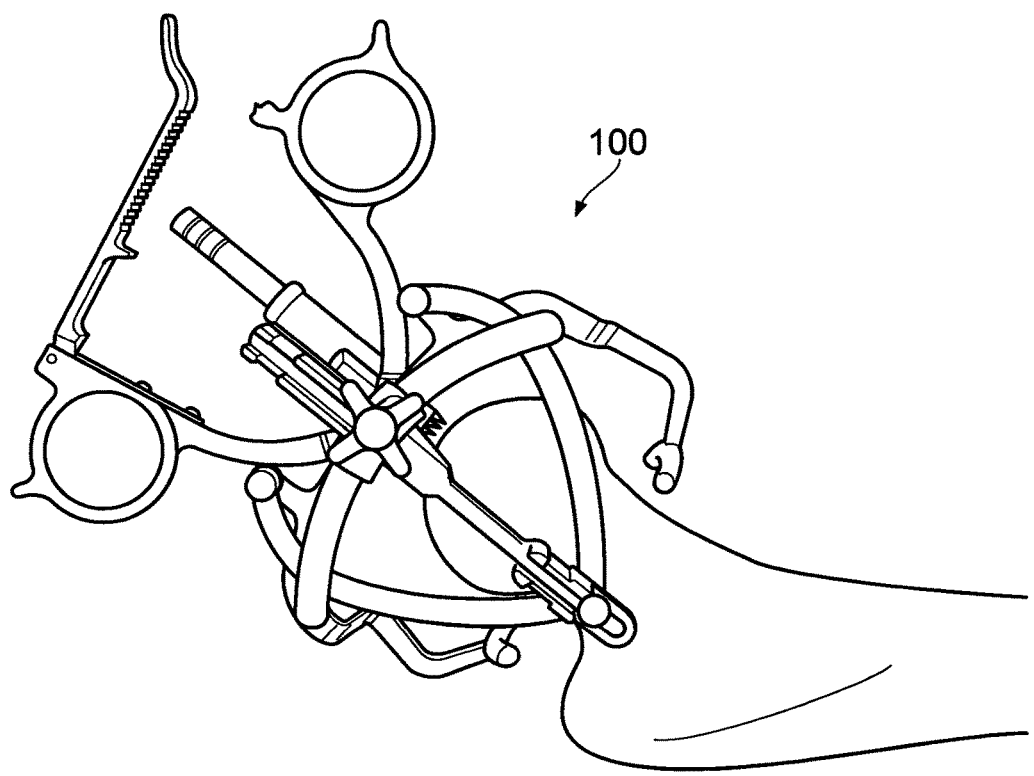
FIGS. 28 to 38 show various stages of operation of a device according to an embodiment of the present invention.
Figure 29:
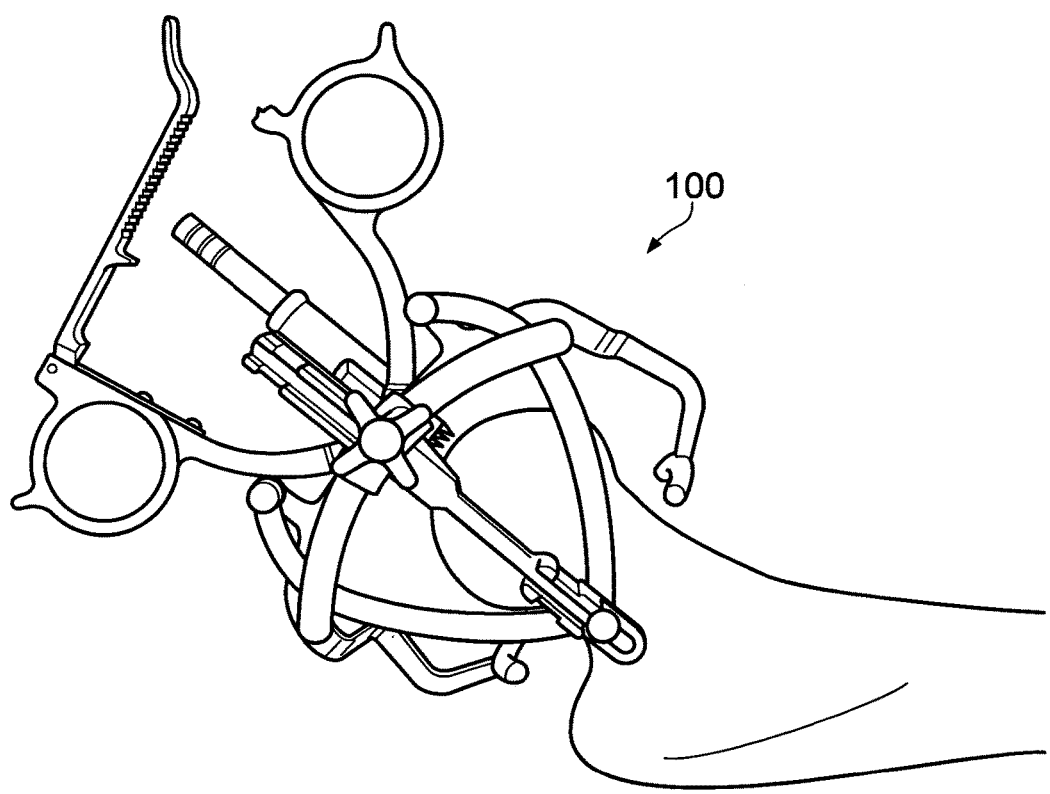
Figure 30:
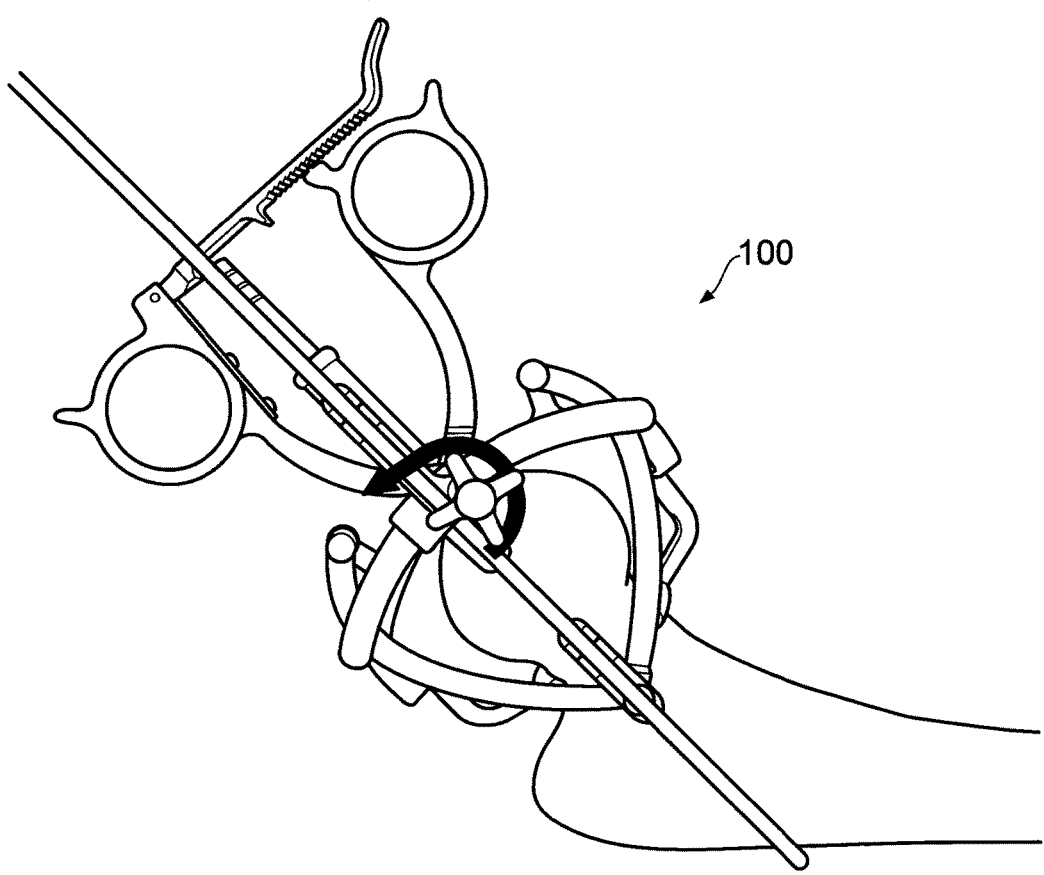
Figure 31:
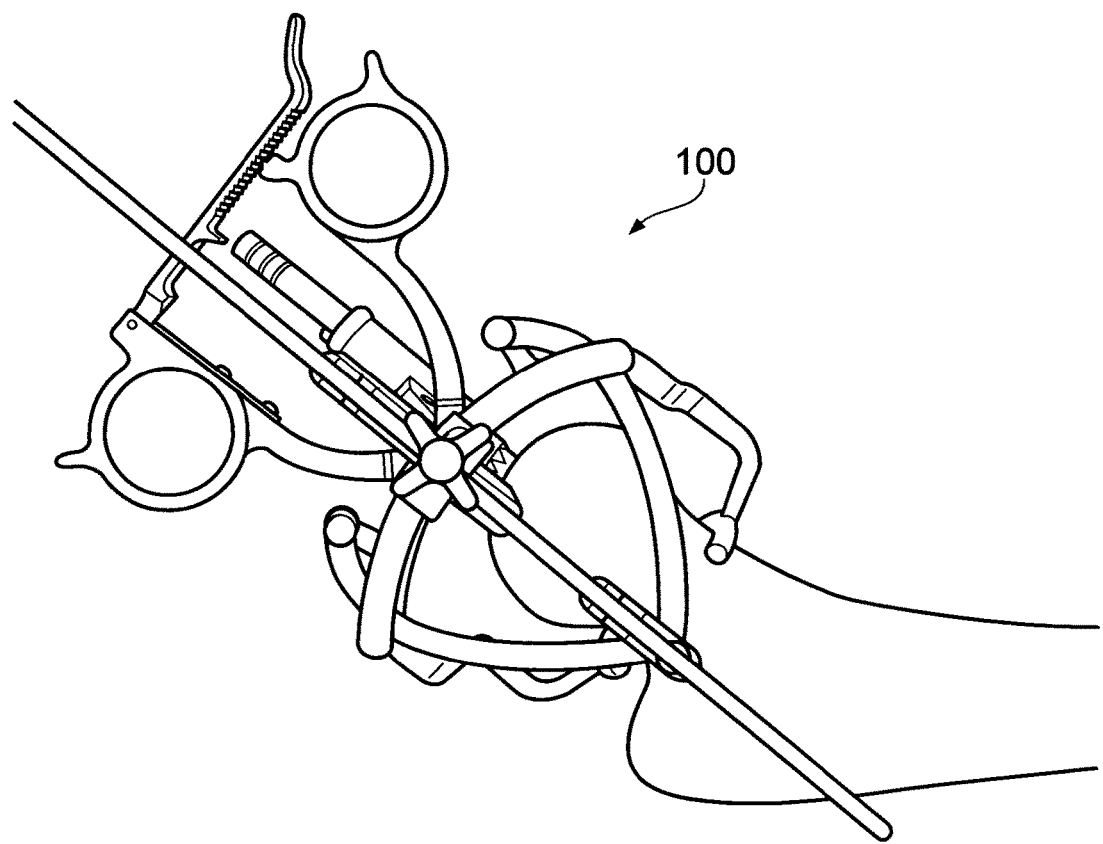
Figure 32:
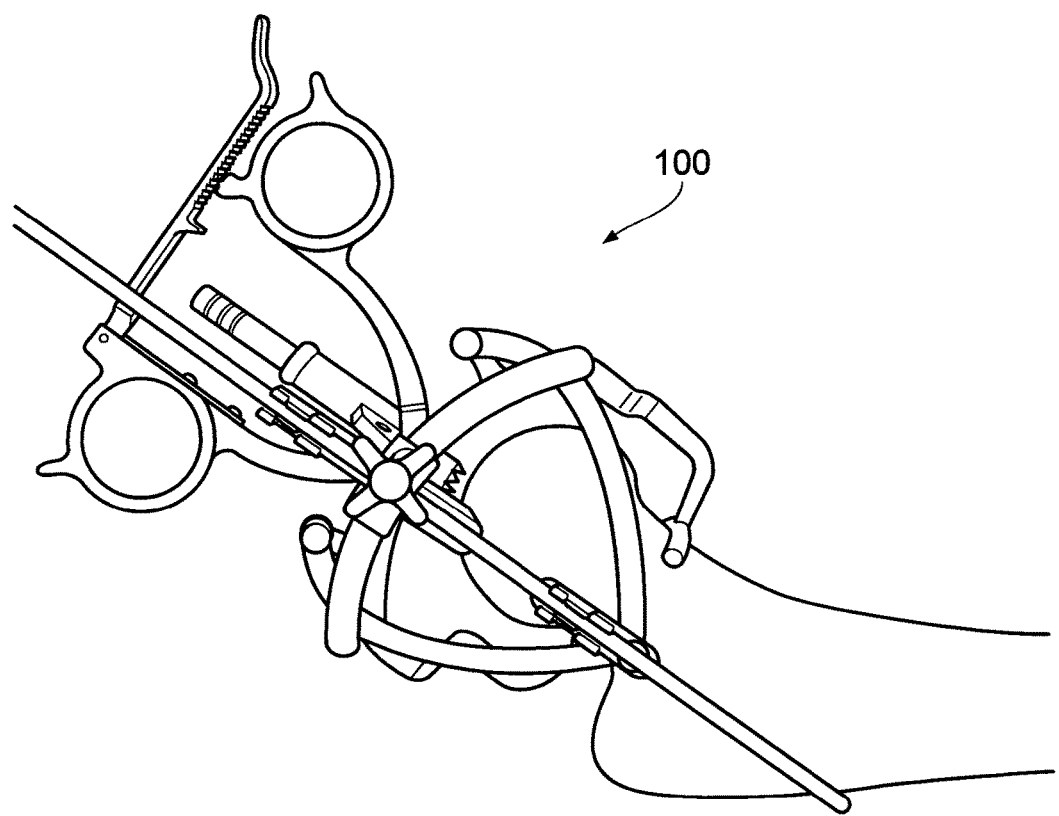
Figure 33:
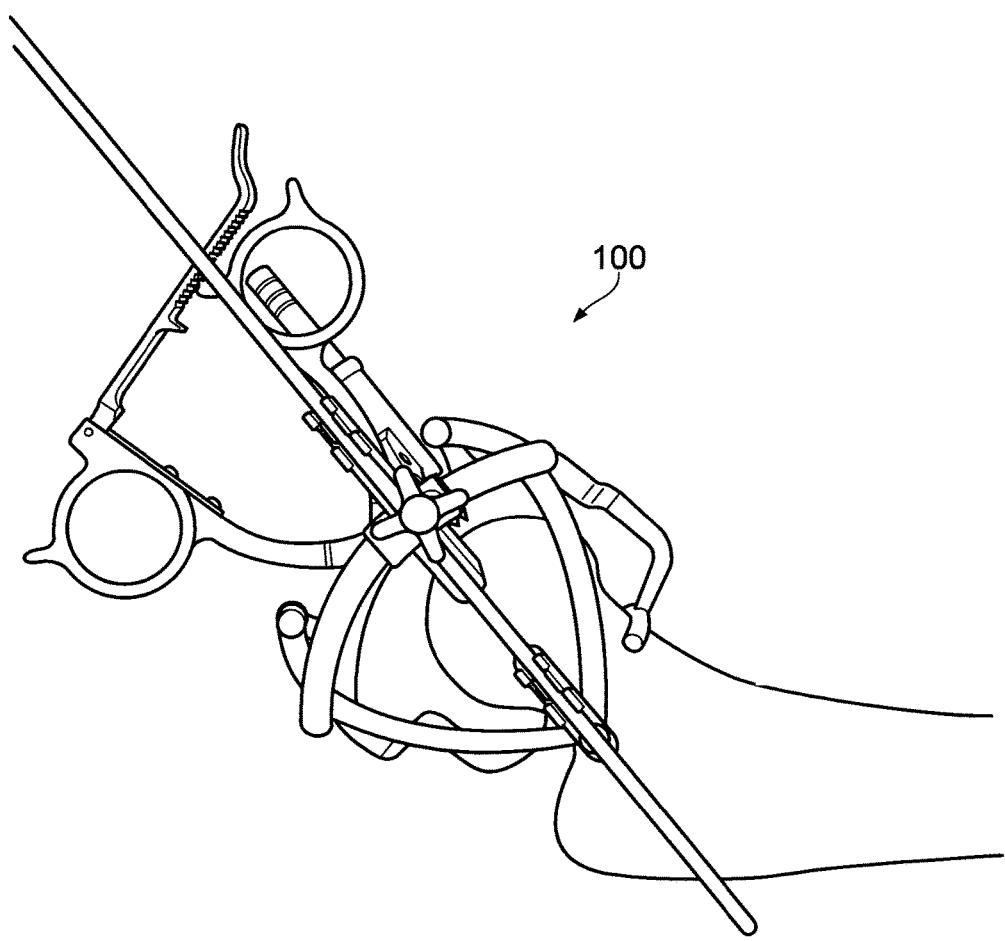
Figure 34:
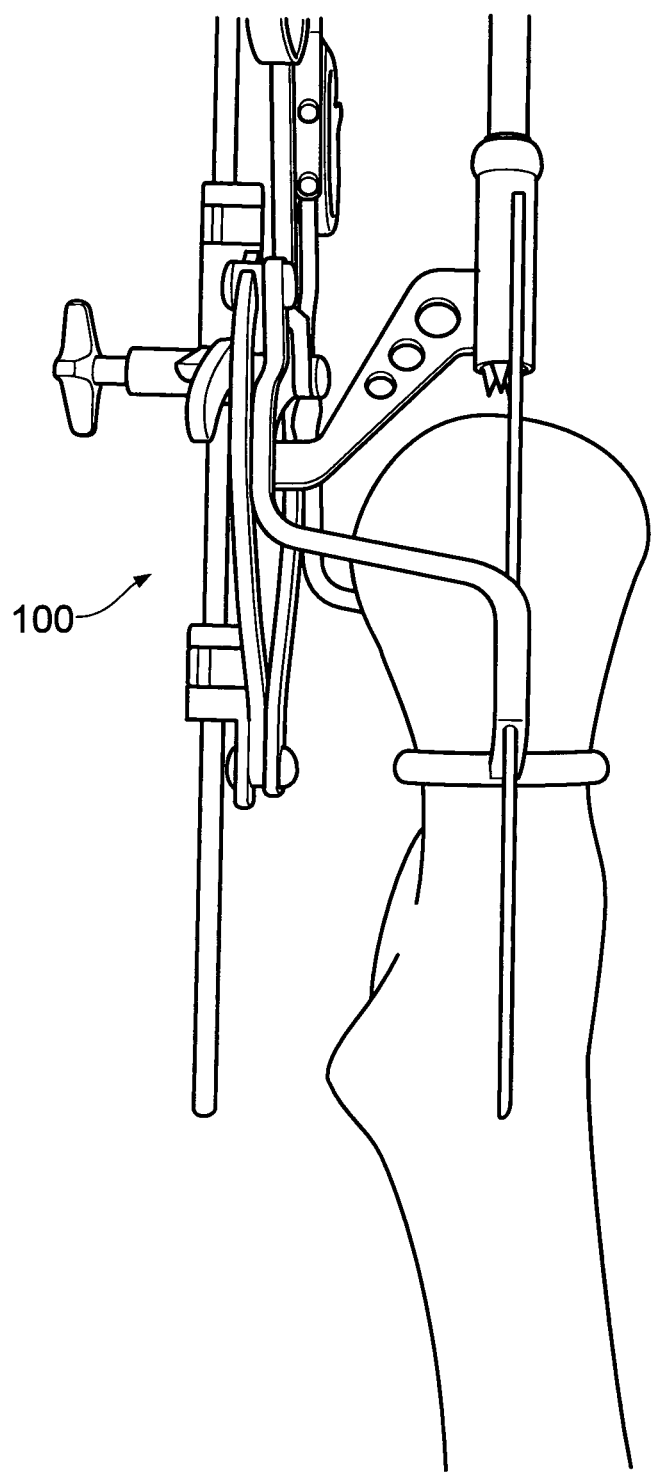
Figure 35:
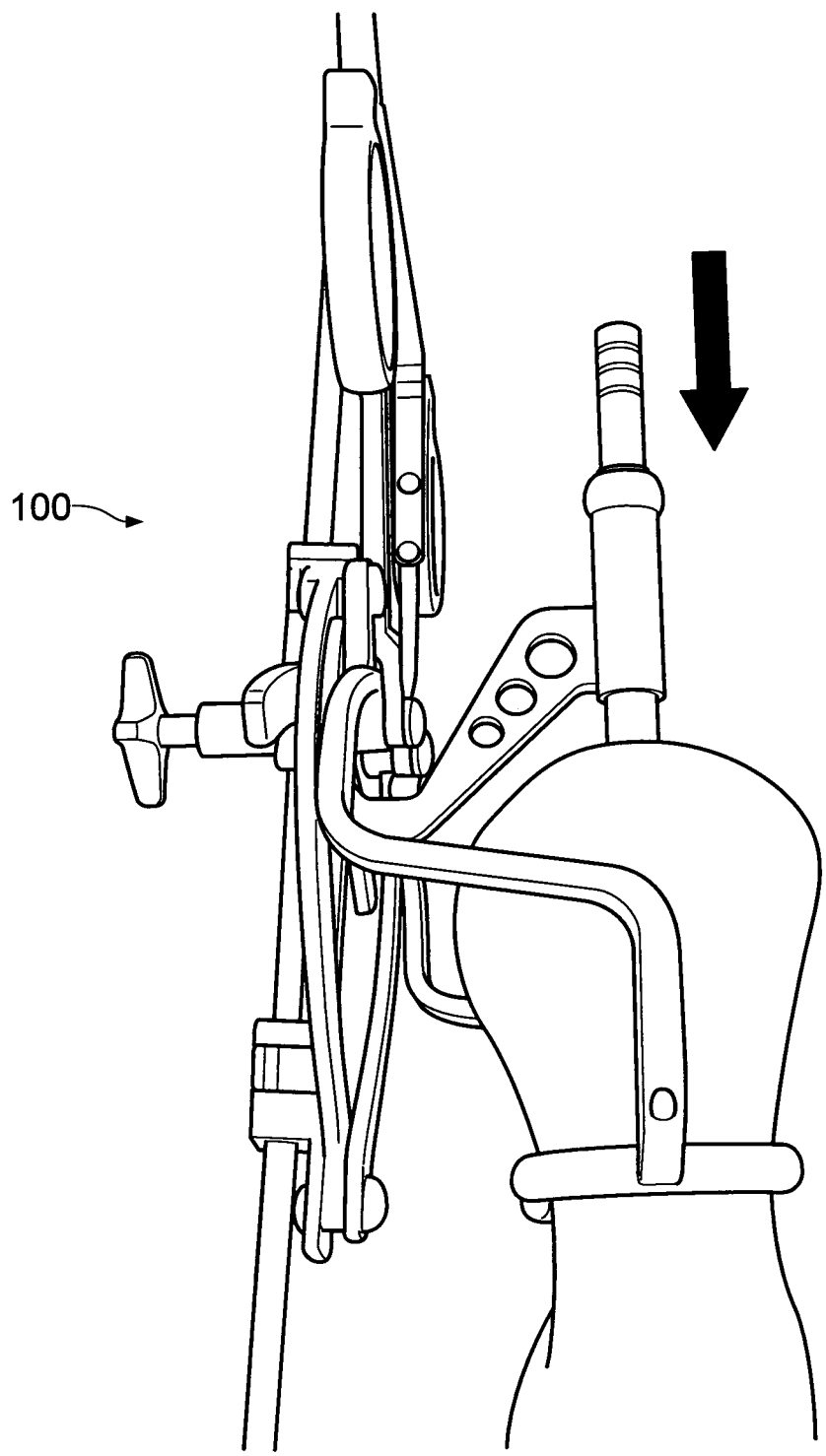
Figure 36:
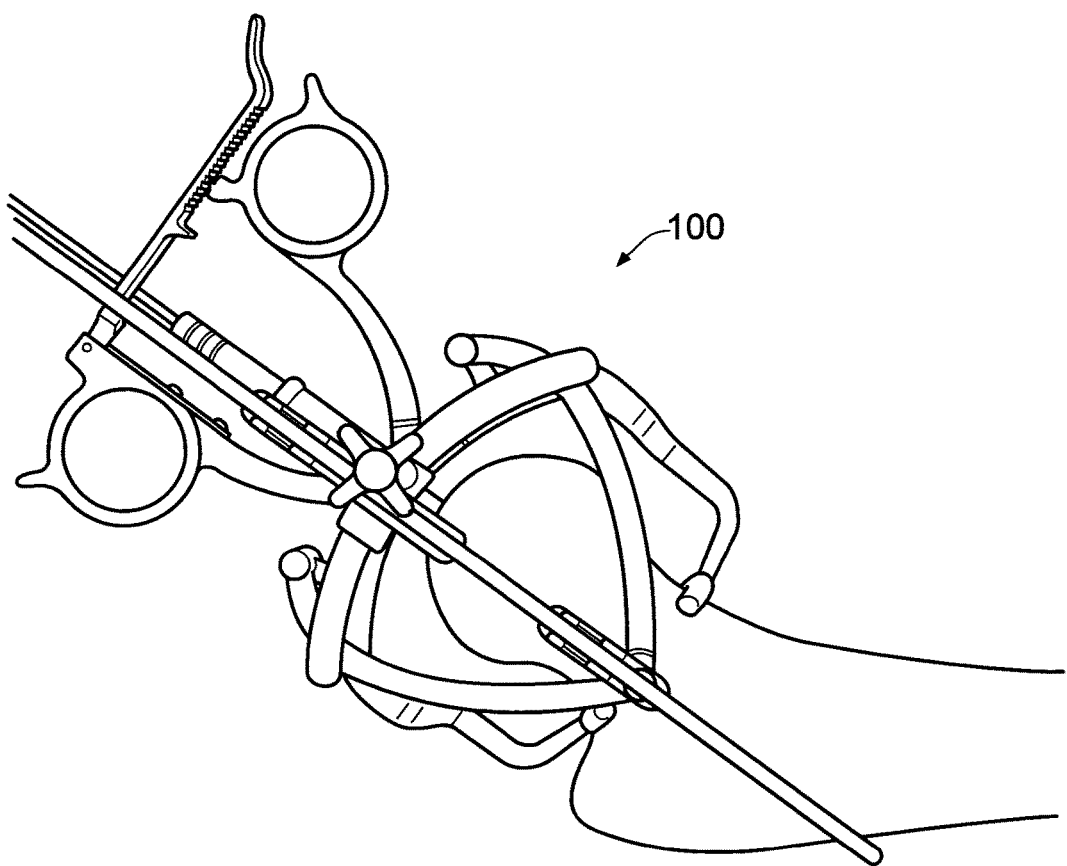
Figure 37:
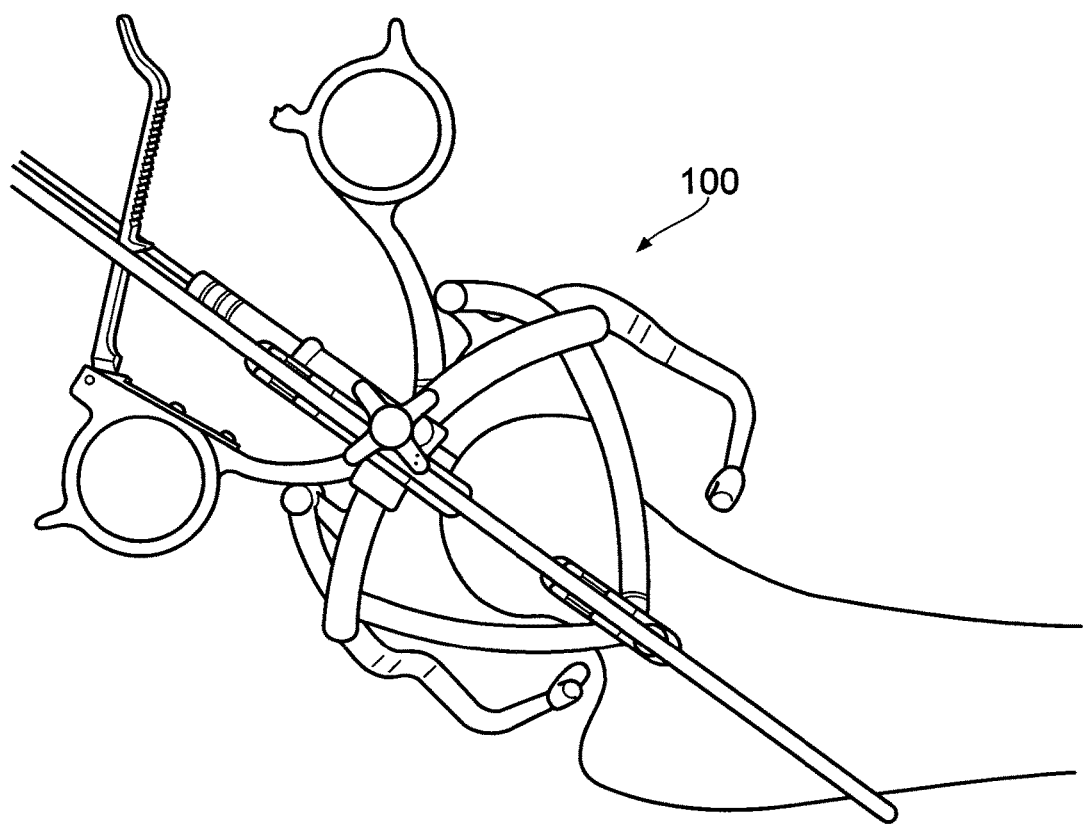
Figure 38:
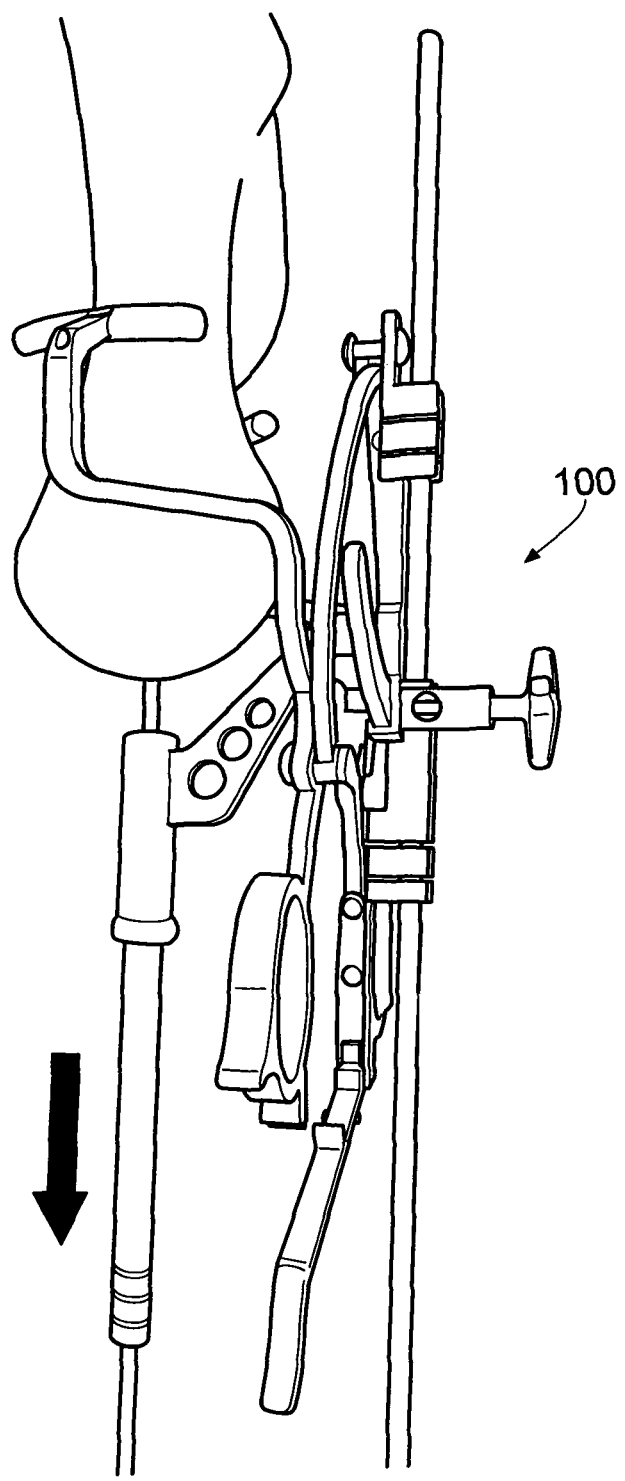

FIG. 27 shows a device (100) that is very similar to the device (1) shown in FIGS. 1 to 10. Accordingly, corresponding parts are labelled the same as those in FIGS. 1 to 10. In contrast to device (1), device (100) only has one leaf spring (19), as opposed to two. As for device (1), the leaf spring (19) of device (100) biases the proximal ends (6,7) apart and hence biases distal ends (10,11) apart. Furthermore, device (100) has a goneometer in the form of a linear rod (101).

FIGS. 28 to 38 show various stages of operation of the device (100) shown in FIG. 27. As noted above, device (100) is very similar to device (1) and therefore the description supporting FIGS. 17 to 26 applies to the operation of the device (100) shown in FIGS. 28 to 38.

The devices according to the present invention are of a size that is compatible with the dimensions of the bone that is operated on. For example, when used in hip resurfacing, the device is sized so as to be complementary to the dimensions of a femur. Devices according to the present invention may be sized so that they are suitable for minimally invasive surgery.

Referring to FIG. 2, the length of the device measured from the ratchet arm (15) to jaws (12,13) may be in the range 10 to 20 cm. The length may be in the range 10 to 15 cm. Preferably, the length is in the range 11 to 14 cm.

Referring to FIG. 2, the width of the device measured between the outer edges of grips (8,9) may be in the range 7 to 12 cm. The width may be in the range 8 to 11 cm. Preferably, the width is in the range 8 to 10 cm.

Referring to FIG. 4, the depth of the device measured between the pivot (5) and the point at which arm (4) attaches to jaw 13 may be in the range 3 to 6 cm. The depth may be in the range 3 to 5.5 cm. Preferably, the depth is in the range 3 to 5 cm.

Devices according to the present invention may be made of metal. The metal may be stainless steel. The metal may be titanium. The metal may be aluminium. The metal may be an alloy. Preferably, the metal is stainless steel.

Devices according to the present invention may have dimensions and/or be made of materials such that they have some flexibility, enabling enhanced manipulation by the surgeon, particularly in minimally invasive surgery.

The invention claimed is:

1. A device for aligning a guide wire with a bone, comprising:
   an attachment means reversibly attachable to a bone, the attachment means defining an attachment means axis, wherein the attachment means comprises a clamp including two arms, each arm having a proximal end portion including a finger grip, a distal end portion including a jaw, and an intermediate portion connecting the proximal end portion and the distal end portion, wherein the arms are pivotally connected to one another at the intermediate portions, wherein the jaws are opposed to one another and are configured to attach to the bone, wherein the proximal ends enable a user to reversibly attach the opposed jaws to the bone, and wherein the clamp comprises a resilient means for biasing the jaws apart;
   an alignment means connected to the attachment means, the alignment means defining an alignment means axis, the alignment means being moveable so as to locate a portion of the bone for insertion of the guide wire along the alignment means axis and to pivot the alignment means axis with respect to the attachment means axis, wherein the alignment means comprises a centering mechanism for locating the center of the bone, wherein the alignment means is configured to guide the guide wire for insertion along the alignment means axis with the alignment means axis in each of a plurality of orientations relative to the attachment means axis.

2. A device according to claim 1, wherein the alignment means is reversibly connected to the attachment means.

3. A device according to claim 1, wherein the alignment means receives a guide wire, in use.

4. A device according to claim 1, wherein the alignment means comprises:
   an alignment guide for receiving, in use, at least one of a goneometer and a guide wire; and
   a support arm connected to the attachment means, wherein the alignment guide is moveably connected to the support arm.

5. A device according to claim 4, wherein the alignment guide is reversibly connected to the support arm.

6. A device according to claim 4, wherein the support arm is reversibly connected to the attachment means.

7. A device according to claim 4, wherein the support arm is pivotally connected to the attachment means.

8. A device according to claim 4, wherein the alignment guide comprises a drill guide.

9. A device according to claim 1, wherein the centering mechanism is reversibly connected to the attachment means.

10. A device according to claim 1, wherein the centering mechanism comprises two moveable arms, each arm having a proximal end and a distal end, the arms being pivotally connected together at their distal ends, the arms being pivotally connected to the attachment means at their proximal ends, and wherein, in use, the pivot connection between the distal ends of the arms locates the center of the bone.

11. A device according to claim 10, wherein the alignment guide is pivotally connected to the distal ends of the centering mechanism arms.

12. A device according to claim 1, wherein the clamp comprises a self-locking mechanism.

13. A device according to claim 12, wherein the self-locking mechanism is a ratchet mechanism having a release means for unlocking the clamp.

14. A device according to claim 1, wherein the resilient means is a spring.

15. A device according to claim 1, further comprising a fixation means.

16. A device according to claim 15, wherein the fixation means comprises at least one retractable spike.

17. A device according to claim 16, wherein the fixation means comprises a retractable spiked tube.

18. A device for aligning a tool with a bone, the device comprising:
   an attachment mechanism configured for releasable attachment to the bone, the attachment mechanism comprising a clamp, wherein the clamp includes a pair of clamp arms, and wherein the clamp arms are pivotally connected to one another at a first pivot;
   a centering mechanism comprising a pair of centering arms, wherein each of the centering arms has a first end connected to the attachment mechanism and a second end connected to a second pivot, wherein a clamp axis is defined through the first pivot and the second pivot; and
   an alignment device connected to the attachment mechanism, wherein the alignment device includes an alignment guide defining an alignment guide axis, and wherein the alignment guide is movable such that the alignment guide axis is pivotable with respect to the clamp axis.

19. The device of claim 18, wherein the alignment device further comprises a support arm, wherein the alignment guide includes a first portion movably mounted to the support arm and a second portion pivotally mounted to the second pivot, and wherein the alignment guide axis is defined through the first portion and the second portion.

20. The device of claim 18, wherein a first centering arm of the pair of centering arms is pivotally connected to a first clamp arm of the pair of clamp arms at a third pivot, and wherein a second centering arm of the pair of centering arms is pivotally connected to a second clamp arm of the pair of clamp arms at a fourth pivot.

21. The device of claim 18, wherein the centering arms are pivotable about a pivot axis defined by the second pivot, wherein each of the clamp arms includes a corresponding jaw, wherein the jaws have a center point defined therebetween, and wherein the center point of the jaws is defined along the pivot axis defined by the second pivot.

22. A device for aligning a guide wire with a bone, comprising:
   an attachment means reversibly attachable to a bone, the attachment means defining an attachment means axis, wherein the attachment means comprises a clamp including two arms, each arm having a proximal end portion including a finger grip, a distal end portion including a jaw, and an intermediate portion connecting the proximal end portion and the distal end portion, wherein the arms are pivotally connected to one another at the intermediate portions, wherein the jaws are opposed to one another and are configured to attach to the bone, wherein the proximal ends enable a user to reversibly attach the opposed jaws to the bone, and wherein the clamp comprises a resilient means for biasing the jaws apart;
   an alignment means connected to the attachment means, the alignment means defining an alignment means axis, the alignment means being moveable so as to locate a portion of the bone for insertion of the guide wire along the alignment means axis and to pivot the alignment means axis with respect to the attachment means axis, wherein the alignment means comprises a centering mechanism for locating the center of the bone;
   wherein the alignment means comprises a support arm mounted to the attachment means, and an alignment guide including a first end portion and an opposite second end portion; and
   wherein the centering mechanism is movably mounted to the attachment means, wherein the centering mechanism comprises a pair of centering arms, and wherein the centering arms are pivotably connected to one another and to the second end portion of the alignment guide via a pivot defining a pivot axis.

23. The device of claim 22, wherein the first end portion of the alignment guide is movably mounted to the support arm; and
   wherein the alignment guide is operable to pivot about the pivot axis defined at the second end portion.

* * * * *